(12) United States Patent
Youngman

(10) Patent No.: US 9,714,252 B2
(45) Date of Patent: Jul. 25, 2017

(54) CYCLIC SULFONAMIDES AS SODIUM CHANNEL BLOCKERS

(71) Applicant: Purdue Pharma L.P., Stamford, CT (US)

(72) Inventor: Mark Andrew Youngman, North Wales, PA (US)

(73) Assignee: Purdue Pharma L.P., Stamford, CT (US)

( * ) Notice: Subject to any disclaimer, the term of this patent is extended or adjusted under 35 U.S.C. 154(b) by 29 days.

(21) Appl. No.: 14/653,471

(22) PCT Filed: Dec. 18, 2013

(86) PCT No.: PCT/IB2013/002840
§ 371 (c)(1),
(2) Date: Jun. 18, 2015

(87) PCT Pub. No.: WO2014/096941
PCT Pub. Date: Jun. 26, 2014

(65) Prior Publication Data
US 2015/0336974 A1 Nov. 26, 2015

Related U.S. Application Data

(60) Provisional application No. 61/740,166, filed on Dec. 20, 2012.

(51) Int. Cl.
| | |
|---|---|
| C07D 491/107 | (2006.01) |
| C07D 417/04 | (2006.01) |
| A61K 31/428 | (2006.01) |
| C07D 417/14 | (2006.01) |
| C07D 491/10 | (2006.01) |
| G01N 33/60 | (2006.01) |
| G01N 33/68 | (2006.01) |

(52) U.S. Cl.
CPC ....... *C07D 491/107* (2013.01); *C07D 417/04* (2013.01); *C07D 417/14* (2013.01); *C07D 491/10* (2013.01); *G01N 33/60* (2013.01); *G01N 33/6872* (2013.01); *G01N 2500/02* (2013.01)

(58) Field of Classification Search
CPC C07D 491/107; C07D 417/04; C07D 417/14; C07D 491/10; G01N 33/60; A61K 31/428
USPC .............................................. 546/15; 514/359
See application file for complete search history.

(56) References Cited

U.S. PATENT DOCUMENTS

| | | | |
|---|---|---|---|
| 4,555,520 A | 11/1985 | Misra et al. | |
| 6,040,311 A | 3/2000 | Duggan et al. | |
| 6,281,211 B1 | 8/2001 | Cai et al. | |
| 6,335,354 B2 | 1/2002 | Hogenkamp | |
| 6,339,045 B1 | 1/2002 | Kanno et al. | |
| 6,414,011 B1 | 7/2002 | Hogenkamp et al. | |
| 6,479,484 B1 | 11/2002 | Lan et al. | |
| 6,500,825 B2 | 12/2002 | Lan et al. | |
| 6,613,803 B1 | 9/2003 | Wang et al. | |
| 6,638,947 B2 | 10/2003 | Wang et al. | |
| 6,696,442 B2 | 2/2004 | Wang et al. | |
| 6,737,418 B2 | 5/2004 | Hogenkamp et al. | |
| 6,770,661 B2 | 8/2004 | Shao et al. | |
| 6,867,210 B2 | 3/2005 | Hogenkamp et al. | |
| 6,919,363 B2 | 7/2005 | Hogenkamp et al. | |
| 7,022,714 B2 | 4/2006 | Sun et al. | |
| 7,078,426 B2 | 7/2006 | Hogenkamp et al. | |
| 7,091,210 B2 | 8/2006 | Lan et al. | |
| 7,105,549 B2 | 9/2006 | Shao et al. | |
| 7,169,782 B2 | 1/2007 | Sun et al. | |
| 7,229,993 B2 | 6/2007 | Goehring et al. | |
| 7,393,872 B2 | 7/2008 | Lan et al. | |
| 7,541,465 B2 | 6/2009 | Lan et al. | |
| 7,579,367 B2 | 8/2009 | Shao et al. | |

(Continued)

FOREIGN PATENT DOCUMENTS

| | | |
|---|---|---|
| DE | 2846330 | 11/1979 |
| EP | 1724278 | 11/2006 |

(Continued)

OTHER PUBLICATIONS

Anger. T., et al., "Medicinal Chemistry of Neuronal Voltage-Gated Sodium Channel Blockers," J. Med. Chem. 44(2):115-137, American Chemical Society, United States (2001).

(Continued)

*Primary Examiner* — Rita Desai
(74) *Attorney, Agent, or Firm* — Purdue Pharma L.P.; Alan L. Koller; Weiying Yang

(57) ABSTRACT

The present disclosure provides cyclic sulfonamides of Formula (I), and the pharmaceutically acceptable salts and solvates thereof, wherein $R^1$, $R^2$, $R^{3a}$, $R^{3b}$, and n are defined as set forth in the specification. The present disclosure is also directed to the use of compounds of Formula (I) to treat a disorder responsive to the blockade of sodium channels. For example, compounds of the present disclosure are useful for treating pain.

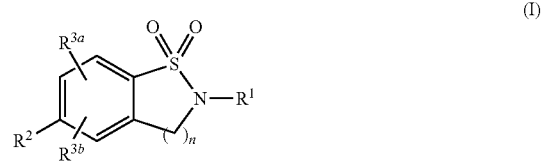

(I)

21 Claims, No Drawings

(56) References Cited

U.S. PATENT DOCUMENTS

| | | |
|---|---|---|
| 7,872,127 B2 | 1/2011 | Lan et al. |
| 7,943,643 B2 | 5/2011 | Shao et al. |
| 8,426,431 B2 | 4/2013 | Lan et al. |
| 9,045,435 B2 | 6/2015 | Goehring et al. |
| 9,120,752 B2 | 9/2015 | Kyle et al. |
| 9,120,786 B2 | 9/2015 | Yu et al. |
| 2002/0037926 A1 | 3/2002 | Lan |
| 2003/0055088 A1 | 3/2003 | Shao et al. |
| 2003/0073724 A1 | 4/2003 | Shao et al. |
| 2003/0125339 A1 | 7/2003 | Chen et al. |
| 2003/0225080 A1 | 12/2003 | Wang et al. |
| 2004/0097569 A1 | 5/2004 | Sun et al. |
| 2004/0122237 A1 | 6/2004 | Amiri et al. |
| 2004/0152696 A1 | 8/2004 | Sun et al. |
| 2004/0176364 A1 | 9/2004 | Sun et al. |
| 2004/0176374 A1 | 9/2004 | Wunberg |
| 2004/0192691 A1 | 9/2004 | Hogenkamp et al. |
| 2005/0031651 A1 | 2/2005 | Gervais et al. |
| 2005/0043305 A1 | 2/2005 | Hogenkamp et al. |
| 2005/0222027 A1 | 10/2005 | Chiang et al. |
| 2005/0234109 A1 | 10/2005 | Yasukouchi et al. |
| 2006/0089375 A1 | 4/2006 | Allen et al. |
| 2006/0122236 A1 | 6/2006 | Wood et al. |
| 2006/0173050 A1 | 8/2006 | Liu et al. |
| 2006/0241302 A1 | 10/2006 | Kubota et al. |
| 2006/0281763 A1 | 12/2006 | Axon et al. |
| 2007/0072874 A1 | 3/2007 | Cui |
| 2007/0142430 A1 | 6/2007 | Peukert et al. |
| 2008/0032972 A1 | 2/2008 | Dorsey et al. |
| 2008/0139575 A1 | 6/2008 | Lu et al. |
| 2008/0318932 A1 | 12/2008 | Lan |
| 2009/0124654 A1 | 5/2009 | Mjalli et al. |
| 2009/0149439 A1 | 6/2009 | Miyauchi et al. |
| 2010/0056478 A1 | 3/2010 | Desarbre et al. |
| 2010/0137606 A1 | 6/2010 | Kiso et al. |
| 2011/0136831 A1 | 6/2011 | Oda et al. |
| 2013/0012485 A1 | 1/2013 | Baeschlin et al. |
| 2013/0289044 A1 | 10/2013 | Goehring et al. |
| 2013/0296281 A1 | 11/2013 | Kyle et al. |
| 2013/0303526 A1 | 11/2013 | Ni et al. |
| 2013/0303568 A1 | 11/2013 | Lan et al. |
| 2013/0345211 A1 | 12/2013 | Kyle et al. |
| 2014/0005212 A1 | 1/2014 | Ni et al. |
| 2014/0249128 A1 | 9/2014 | Tadesse et al. |
| 2014/0288092 A1 | 9/2014 | Yao et al. |
| 2014/0303139 A1 | 10/2014 | Ni et al. |
| 2014/0309228 A1 | 10/2014 | Engel |
| 2014/0315783 A1 | 10/2014 | Shao |
| 2015/0045397 A1 | 2/2015 | Tafesse et al. |
| 2015/0057300 A1 | 2/2015 | Tafesse et al. |
| 2015/0133500 A1 | 5/2015 | Tafesse et al. |
| 2015/0141434 A1 | 5/2015 | Park |
| 2015/0250789 A1 | 9/2015 | Goehring et al. |
| 2015/0284383 A1 | 10/2015 | Lynch et al. |
| 2015/0353512 A1 | 12/2015 | Tadesse et al. |
| 2016/0009659 A1 | 1/2016 | Lockman et al. |
| 2016/0024022 A1 | 1/2016 | Ni et al. |
| 2016/0243129 A1 | 8/2016 | Lautermilch |
| 2016/0326111 A1 | 11/2016 | Kyle |

FOREIGN PATENT DOCUMENTS

| | | |
|---|---|---|
| JP | 2008115166 | 5/2008 |
| WO | WO-96/32940 | 10/1996 |
| WO | WO-98/47869 | 10/1998 |
| WO | WO-99/26614 | 6/1999 |
| WO | WO-00/57877 | 10/2000 |
| WO | WO-01/68612 | 9/2001 |
| WO | WO-01/72714 | 10/2001 |
| WO | WO-02/100849 | 12/2002 |
| WO | WO-03/022276 | 3/2003 |
| WO | WO-03/022285 | 3/2003 |
| WO | WO-03/059871 | 7/2003 |
| WO | WO-03/082272 | 10/2003 |
| WO | WO-2004/014844 | 2/2004 |
| WO | WO-2004/016592 | 2/2004 |
| WO | WO-2004/062553 | 7/2004 |
| WO | WO-2004/089308 | 10/2004 |
| WO | WO-2006/063167 | 6/2006 |
| WO | WO-2006/068410 | 6/2006 |
| WO | WO-2006/105222 | 10/2006 |
| WO | WO-2006/110917 | 10/2006 |
| WO | WO-2007/021941 | 2/2007 |
| WO | WO-2007/047474 | 4/2007 |
| WO | WO-2007/050522 | 5/2007 |
| WO | WO-2007/083239 | 7/2007 |
| WO | WO-2008/044217 | 4/2008 |
| WO | WO-2008/068470 | 6/2008 |
| WO | WO-2008/097991 | 8/2008 |
| WO | WO-2008/135826 | 11/2008 |
| WO | WO-2009/001730 | 12/2008 |
| WO | WO-2009/103032 | 8/2009 |
| WO | WO-2009/147440 | 12/2009 |
| WO | WO-2010/010380 | 1/2010 |
| WO | WO-2010/051188 | 5/2010 |
| WO | WO-2010/121164 | 10/2010 |
| WO | WO-2012/007836 | 1/2012 |
| WO | WO-2012/035421 | 3/2012 |
| WO | WO-2012/085650 | 6/2012 |
| WO | WO-2013/030665 | 3/2013 |
| WO | WO-2013/064883 | 5/2013 |
| WO | WO-2013/072758 | 5/2013 |
| WO | WO-2013064884 | 5/2013 |
| WO | WO-2013/136170 | 9/2013 |
| WO | WO-2014/135955 A1 | 9/2014 |
| WO | WO-2014/151393 A2 | 9/2014 |
| WO | WO-2015/031036 A1 | 3/2015 |
| WO | WO-2015/094443 A1 | 6/2015 |
| WO | WO-2015/099841 A1 | 7/2015 |
| WO | WO-2015/100174 A1 | 7/2015 |
| WO | WO-2015/112801 A1 | 7/2015 |

OTHER PUBLICATIONS

Baker, M.D. and Wood, J.N., "Involvement of Na+ channels in pain pathways," Trends Pharmacol. Sci. 22(1):27-31, Elsevier Science Ltd., England (2001).

Black, J.A., et al., "Sensory neuron-specific sodium channel SNS is abnormally expressed in the brains of mice with experimental allergic encephalomyelitis and humans with multiple sclerosis," Proc. Natl. Acad. Sci. USA 97(21):11598-11602, National Academy of Sciences, United States (2000).

Brown, C.M., et al., "Neuroprotective properties of lifarizine compared with those of other agents in a mouse model of focal cerebral ischaemia," Br. J. Pharmacol. 115(8):1425-1432, Stockton Press, England (1995).

Cannon, S.C. "Spectrum of Sodium Channel disturbances in the Nondystrophic myotonias and periodic paralyses," Kidney Int. 57(3):772-779, Int. Soc of Neprohlogy, US (2000).

Catterall, W.A., "Common modes of drug action on Na+ channels: local anesthetics, antiarrhythmics and anticonvulsants," Trends Pharmacol. Sci. 8:57-65, Elsevier Science Publishers, B.V., Netherlands (1987).

Chahine, M., et al., "Voltage-Gated Sodium Channels in Neurological Disorders," CNS Neurol. Disord. Drug Targets 7 (2):144-158, Bentham Science Publishers Ltd.,United Arab Emirates (2008).

Clare, J.J., et al., "Voltage-gated sodium channels as therapeutic targets," Drug Discov. Today 5(11):506-520, Elsevier Science Ltd., England (2000).

Donaldson, I., "Tegretol: a double blind trial in tinnitus," J. Laryngol. Otol. 95(9):947-951, Cambridge University Press, England (1981).

Graham, S.H., et al., "Neuroprotective Effects of a Use-Dependent Blocker of Voltage-Dependent Sodium Channels, BW619C89, in Rat Middle Cerebral Artery Occlusion," J. Pharmacol. Exp. Ther. 269(2):854-859, The American Society for Pharmacology and Experimental Therapeutics, United States (1994).

Hubner, C., et al., "Ion Channel Diseases," Human Molecular Genetics 11:2435-2445, Oxford University Press (2002).

(56) References Cited

OTHER PUBLICATIONS

International Search Report for International Patent Application No. PCT/IB2013/002840, mailed Feb. 19, 2014, European Patent Office, Rijswijk, Netherlands.

Kyle, D.J., and Ilyin, V.I., "Sodium Channel Blockers," J. Med. Chem. 50(11):2583-2588, American Chemical Society, United States (2007).

Lai, J., et al., "Voltage-Gated Sodium Channels and Hyperalgesia," Annu. Rev. Pharmacol. Toxicol. 44:371-397, Annual Reviews, United States (2004).

Laird, J.M.A., et al., "Deficits in Visceral Pain and Referred Hyperalgesia in Nav1.8 (SNS/PN3)-Null Mice," J. Neurosci. 22(19):8352-8356, Society for Neuroscience, United States (2002).

Liu, H., et al., "Mutations in Cardiac Sodium Channels: Clinical Implications," Am. J. Pharmacogenomics 3(3):173-179, Adis Data Information BV, New Zealand (2003).

Majumdar, B., et al., "An electrocochleographic study of the effects of lignocaine on patients with tinnitus," Clin. Otolaryngol. Allied Sci. 8(3):175-180, Blackwell Scientific Publications, England (1983).

Meisler, M.H. and Kearney, J.A., "Sodium channel mutations in epilepsy and other neurological disorders," J. Clin. Invest. 115(8):2010-2017, American Society for Clinical Investigation, United States (2005).

Moller, A., "Similarities Between Chronic Pain and Tinnitus," The American Journal of Ontology 18:577-585 (1997).

Nassar, M.A., et al., "Nociceptor-specific gene deletion reveals a major role for Nav1.7 (PN1) in acute and inflammatory pain," Proc. Natl. Acad. Sci. USA 101(34):12706-12711, National Academy of Sciences, United States (2004).

Noble, D., "Unraveling the genetics and mechanisms of cardiac arrhythmia," Proc. Natl. Acad. Sci. USA 99(9):5755-5756, National Academy of Sciences, United States (2002).

Srivatsa, U., et al., "Mechanisms of Antiarrhythmic Drug Actions and Their Clinical Relevance for Controlling Disorders of Cardiac Rhythm," Curr. Cardiol. Rep. 4(6):401-410, Current Science Inc., United States (2002).

Taylor, C.P. and Meldrum, B.S., "Na+ channels as targets for neuroprotective drugs," Trends Pharmacol. Sci. 16(9):309-316, Elsevier Science Ltd., England (1995).

Toledo-Aral, J.J., et al., "Identification of PN1, a predominant voltage-dependent sodium channel expressed principally in peripheral neurons," Proc. Natl. Acad. Sci. USA 94(4):1527-1532, The National Academy of Sciences, United States (1997).

Tonndorf, J., "The analogy between tinnitus and pain: A suggestion for physiological basis of chronic tinnitus," Hearing Research 28(2-3):271-275, Elsevier Science Publishers B.V., Netherlands (1987).

Wood, J.N., et al., "Voltage-Gated Sodium Channels and Pain Pathways," J. Neurobiol. 61(1):55-71, Wiley Periodicals, Inc., United States (2004).

Yogeeswari, P., et al., "Ion Channels as Important Targets for Antiepileptic Drug Design," Curr. Drug Targets 5 (7):589-602, Bentham Science Publishers Ltd., Netherlands (2004).

CYCLIC SULFONAMIDES AS SODIUM CHANNEL BLOCKERS

CROSS-REFERENCE TO RELATED APPLICATIONS

This application is the U.S. national phase, pursuant to 35 U.S.C. §371, of PCT International Application Ser. No. PCT/IB2013/002840, filed Dec. 18, 2013, designating the United States and published in English on Jun. 26, 2014 as PCT Publication No. WO 2014/096941 A1, which claims priority to U.S. Provisional Application Ser. No. 61/740,166, filed Dec. 20, 2012. The contents of the afore-mentioned patent applications are incorporated herein by their entirety.

BACKGROUND OF THE INVENTION

Field of the Invention

This invention is in the field of medicinal chemistry. The invention provides novel cyclic sulfonamides and the use of these compounds as blockers of voltage-gated sodium ($Na^+$) channels.

Background Art

Voltage-gated sodium channels (VGSCs) are found in all excitable cells. Sodium channels are primarily responsible for generating the rapid upstroke of the action potential in neuronal cells of the central nervous system (CNS) and peripheral nervous system (PNS). In this manner sodium channels are essential to the initiation and propagation of electrical signals in the nervous system. Proper function of sodium channels is therefore necessary for normal function of the neuron. Consequently, aberrant sodium channel function is thought to underlie a variety of medical disorders (See Hubner et al., *Hum. Mol. Genet.* 11:2435-2445 (2002) for a general review of inherited ion channel disorders) including epilepsy (Yogeeswari et al, *Curr. Drug Target* 5:589-602 (2004)), arrhythmia (Noble, *Proc. Natl. Acad. Sci. USA* 99:5755-5756 (2002)), myotonia (Cannon, *Kidney Int.* 57:772-779 (2000)), and pain (Wood et al., *J. Neurobiol.,* 61:55-71 (2004)).

VGSCs are composed of one α-subunit, which forms the core of the channel and is responsible for voltage-dependent gating and ion permeation, and several auxiliary β-subunits (see, e.g., Chahine et al., *CNS & Neurological Disorders-Drug Targets* 7:144-158 (2008) and Kyle and Ilyin, *J. Med. Chem.* 50:2583-2588 (2007)). α-Subunits are large proteins composed of four homologous domains. Each domain contains six α-helical transmembrane spanning segments. There are currently nine known members of the family of voltage-gated sodium channel α-subunits. Names for this family include SCNx, SCNAx, and $Na_vx.x$ (see Table 1, below). The VGSC family has been phylogenetically divided into two subfamilies $Na_v1.x$ (all but SCN6A) and $Na_v2.x$ (SCN6A). The $Na_v1.x$ subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v1.5$, HI) is almost exclusively expressed in cardiac tissue and has been shown to underlie a variety of cardiac arrhythmias and other conduction disorders (Liu et al., *Am. J. Pharmacogenomics* 3:173-179 (2003)). Consequently, blockers of $Na_v1.5$ have found clinical utility in treatment of such disorders (Srivatsa et al., *Curr. Cardiol. Rep.* 4:401-410 (2002)). The remaining TTX-resistant sodium channels, $Na_v1.8$ (SCN10A, PN3, SNS) and $Na_v1.9$ (SCN11A, NaN, SNS2) are expressed in the peripheral nervous system and show preferential expression in primary nociceptive neurons. Human genetic variants of these channels have not been associated with any inherited clinical disorder. However, aberrant expression of $Na_v1.8$ has been found in the CNS of human multiple sclerosis (MS) patients and also in a rodent model of MS (Black et al., *Proc. Natl. Acad. Sci. USA* 97:11598-115602 (2000)). Evidence for involvement in nociception is both associative (preferential expression in nociceptive neurons) and direct (genetic knockout). $Na_v1.8$-null mice exhibited typical nociceptive behavior in response to acute noxious stimulation but had significant deficits in referred pain and hyperalgesia (Laird et al., *J. Neurosci.* 22:8352-8356 (2002)).

TABLE 1

Voltage-gated sodium channel gene family

| Type | Gene Symbol | Tissue Distribution | TTX $IC_{50}$ (nM) | Disease Association | Indications |
| --- | --- | --- | --- | --- | --- |
| $Na_v1.1$ | SCN1A | CNS/PNS | 10 | Epilepsy | Pain, seizures, neurodegeneration |
| $Na_v1.2$ | SCN2A | CNS | 10 | Epilepsy | Epilepsy, neurodegeneration |
| $Na_v1.3$ | SCN3A | CNS | 15 | — | Pain |
| $Na_v1.4$ | SCN4A | Skeletal muscle | 25 | Myotonia | Myotonia |
| $Na_v1.5$ | SCN5A | Heart muscle | 2,000 | Arrhythmia | Arrhythmia |
| $Na_v1.6$ | SCN8A | CNS/PNS | 6 | — | Pain, movement disorders |
| $Na_v1.7$ | SCN9A | PNS | 25 | Erythermalgia | Pain |
| $Na_v1.8$ | SCN10A | PNS | 50,000 | — | Pain |
| $Na_v1.9$ | SCN11A | PNS | 1,000 | — | Pain |

The $Na_v1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA* 94:1527-1532 (1997)).

An increasing body of evidence suggests that $Na_v1.7$ plays a key role in various pain states, including acute, inflammatory and/or neuropathic pain. Deletion of the SCN9A gene in nociceptive neurons of mice led to an increase in mechanical and thermal pain thresholds and reduction or abolition of inflammatory pain responses (Nassar et al., *Proc. Natl. Acad. Sci. USA* 101:12706-12711 (2004)).

Sodium channel-blocking agents have been reported to be effective in the treatment of various disease states, and have found particular use as local anesthetics, e.g., lidocaine and bupivacaine, and in the treatment of cardiac arrhythmias, e.g., propafenone and amiodarone, and epilepsy, e.g., lamotrigine, phenytoin and carbamazepine (see Clare et al., *Drug Discovery Today* 5:506-510 (2000); Lai et al., *Annu. Rev. Pharmacol. Toxicol.* 44:371-397 (2004); Anger et al., *J. Med. Chem.* 44:115-137 (2001), and Catterall, *Trends Pharmacol. Sci.* 8:57-65 (1987)). Each of these agents is believed to act by interfering with the rapid influx of sodium ions.

Other sodium channel blockers such as BW619C89 and lifarizine have been shown to be neuroprotective in animal models of global and focal ischemia (Graham et al., *J. Pharmacol. Exp. Ther.* 269:854-859 (1994); Brown et al., *British J. Pharmacol.* 115:1425-1432 (1995)).

It has also been reported that sodium channel-blocking agents can be useful in the treatment of pain, including acute, chronic, inflammatory, neuropathic, and other types of pain such as rectal, ocular, and submandibular pain typically associated with paroxysmal extreme pain disorder; see, for example, Kyle and Ilyin., *J. Med. Chem.* 50:2583-2588 (2007); Wood et al., *J. Neurobiol.* 61:55-71 (2004); Baker et al., *TRENDS in Pharmacological Sciences* 22:27-31 (2001); and Lai et al., *Current Opinion in Neurobiology* 13:291-297 (2003); the treatment of neurological disorders such as epilepsy, seizures, epilepsy with febrile seizures, epilepsy with benign familial neonatal infantile seizures, inherited pain disorders, e.g., primary erthermalgia and paroxysmal extreme pain disorder, familial hemiplegic migraine, and movement disorder; and the treatment of other psychiatric disorders such as autism, cerebellar atrophy, ataxia, and mental retardation; see, for example, Chahine et al., *CNS & Neurological Disorders-Drug Targets* 7:144-158 (2008) and Meisler and Kearney, *J. Clin. Invest.* 115:2010-2017 (2005). In addition to the above-mentioned clinical uses, carbamazepine, lidocaine and phenytoin are used to treat neuropathic pain, such as from trigeminal neuralgia, diabetic neuropathy and other forms of nerve damage (Taylor and Meldrum, *Trends Pharmacol. Sci.* 16:309-316 (1995)). Furthermore, based on a number of similarities between chronic pain and tinnitus, (Moller, *Am. J. Otol.* 18:577-585 (1997); Tonndorf, *Hear. Res.* 28:271-275 (1987)) it has been proposed that tinnitus should be viewed as a form of chronic pain sensation (Simpson, et al., *Tip.* 20:12-18 (1999)). Indeed, lidocaine and carbamazepine have been shown to be efficacious in treating tinnitus (Majumdar, B. et al., *Clin. Otolaryngol.* 8:175-180 (1983); Donaldson, *Laryngol. Otol.* 95:947-951 (1981)).

Many patients with either acute or chronic pain disorders respond poorly to current pain therapies, and the development of resistance or insensitivity to opiates is common. In addition, many of the currently available treatments have undesirable side effects.

In view of the limited efficacy and/or unacceptable side-effects of the currently available agents, there is a pressing need for more effective and safer analgesics that work by blocking sodium channels.

BRIEF SUMMARY OF THE INVENTION

In one aspect, the present disclosure provides cyclic sulfonamides represented by Formula I, below, and the pharmaceutically acceptable salts and solvates thereof, collectively referred to herein as "Compounds of the Invention."

In another aspect, the present disclosure provides the use of Compounds of the Invention as blockers of sodium ($Na^+$) channels.

In another aspect, the present disclosure provides a method of treating a disorder responsive to the blockade of sodium channels in a mammal, comprising administering to the mammal an effective amount of a Compound of the Invention.

In another aspect, the present disclosure provides a method of treating pain (e.g., acute pain, chronic pain, which includes but is not limited to, neuropathic pain, postoperative pain, and inflammatory pain, or surgical pain), comprising administering an effective amount of a Compound of the Invention to a mammal in need of such treatment. Specifically, the present disclosure provides a method for preemptive or palliative treatment of pain by administering an effective amount of a Compound of the Invention to a mammal in need of such treatment.

In another aspect, the present disclosure provides a method of treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, comprising administering an effective amount of a Compound of the Invention to a mammal in need of such treatment.

In another aspect, the present disclosure provides a pharmaceutical composition comprising a Compound of the Invention and one or more pharmaceutically acceptable carriers. The pharmaceutical compositions of the present invention may be formulated as immediate release formulations, or as controlled or sustained release formulations.

In another aspect, the present disclosure provides a pharmaceutical composition capable of treating a disorder responsive to the blockade of sodium ion channels, wherein the pharmaceutical composition comprises an effective amount of a Compound of the Invention in a mixture with one or more pharmaceutically acceptable carriers.

In another aspect, the present disclosure provides a method of modulating sodium channels in a mammal, comprising administering to the mammal an effective amount of at least one Compound of the Invention.

In another aspect, the present disclosure provides Compounds of the Invention for use in treating pain in a mammal, e.g., acute pain, chronic pain (which includes but is not limited to, neuropathic pain, postoperative pain, and inflammatory pain), or surgical pain.

In another aspect, the present disclosure provides Compounds of the Invention for use in treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

In another aspect, the present disclosure provides radio-labeled Compounds of the Invention and the use of such compounds as radioligands in any appropriately selected competitive binding assays and screening methodologies. Thus, the present disclosure further provides a method for screening a candidate compound for its ability to bind to a sodium channel or sodium channel subunit using a radiolabeled Compound of the Invention. In certain embodiments, the compound is radiolabeled with $^{3}H$, $^{11}C$, or $^{14}C$. This competitive binding assay can be conducted using any appropriately selected methodology. In one embodiment, the screening method comprises: i) introducing a fixed concentration of the radiolabeled compound to an in vitro preparation comprising a soluble or membrane-associated sodium channel, subunit or fragment under conditions that permit the radiolabeled compound to bind to the channel, subunit or fragment, respectively, to form a conjugate; ii) titrating the conjugate with a candidate compound; and iii) determining the ability of the candidate compound to displace the radiolabeled compound from said channel, subunit or fragment.

In another aspect, the present disclosure provides a Compound of the Invention for use in the manufacture of a medicament for treating pain in a mammal. In one embodiment, the present disclosure provides the use of a Compound of the Invention in the manufacture of a medicament for palliative or preemptive treatment of pain, such as acute pain, chronic pain, or surgical pain.

In another aspect, the present disclosure provides a Compound of the Invention for use in the manufacture of a medicament for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

The invention still further relates to a kit comprising a container (preferably sterile) containing an effective amount of a Compound of the Invention.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

One aspect of the present disclosure is based on the use of Compounds of the Invention as blockers of $Na^{+}$ channels. In view of this property, Compounds of the Invention are useful for treating disorders responsive to the blockade of sodium ion channels.

In one embodiment, Compounds of the Invention are compounds represented by Formula I:

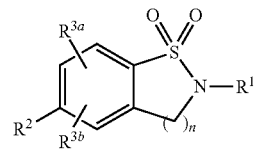

and the pharmaceutically acceptable salts and solvates thereof, wherein:

$R^{1}$ is optionally substituted 5-membered heteroaryl;

$R^{2}$ is selected from the group consisting of:

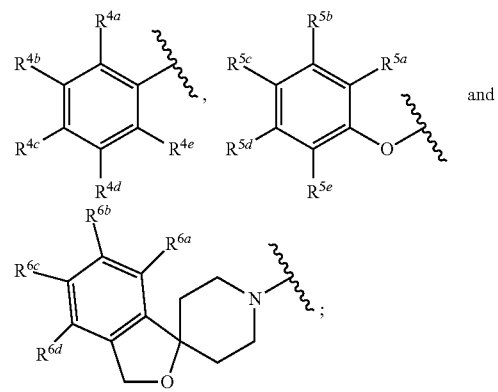

$R^{3a}$ and $R^{3b}$ are each independently selected from the group consisting of hydrogen and halogen;

$R^{4a}$, $R^{4b}$, $R^{4d}$, and $R^{4e}$ are each independently selected from the group consisting of hydrogen, alkyl, halo, nitro, cyano, hydroxy, amino, alkylamino, dialkylamino, haloalkyl, monohydroxyalkyl, dihydroxyalkyl, alkoxy, haloalkoxy, carboxy, and alkoxycarbonyl;

$R^{4c}$ is selected from the group consisting of aryloxy and heteroaryloxy;

$R^{5a}$ is selected from the group consisting of optionally substituted aryl and optionally substituted heteroaryl;

$R^{5b}$, $R^{5c}$, $R^{5d}$, and $R^{5e}$ are each independently selected from the group consisting of hydrogen, alkyl, halo, nitro, cyano, hydroxy, amino, alkylamino, dialkylamino, haloalkyl, monohydroxyalkyl, dihydroxyalkyl, alkoxy, haloalkoxy, carboxy, and alkoxycarbonyl;

$R^{6a}$, $R^{6b}$, $R^{6c}$, and $R^{6d}$ are each independently selected from the group consisting of hydrogen, alkyl, halo, nitro, cyano, hydroxy, amino, alkylamino, dialkylamino, haloalkyl, monohydroxyalkyl, dihydroxyalkyl, alkoxy, haloalkoxy, carboxy, and alkoxycarbonyl; and n is 1, 2, or 3.

In another embodiment, Compounds of the Invention are compounds represented by Formula I, and the pharmaceutically acceptable salts and solvates thereof, wherein $R^{3a}$ and $R^{3b}$ are hydrogen, and $R^{1}$, $R^{2}$ and n are as defined above in connection with Formula I.

In another embodiment, Compounds of the Invention are compounds represented by Formula I, and the pharmaceutically acceptable salts and solvates thereof, wherein n is 1, and $R^{1}$, $R^{2}$, $R^{3a}$ and $R^{3b}$ are as defined above in connection with Formula I.

In another embodiment, Compounds of the Invention are compounds represented by Formula I, and the pharmaceutically acceptable salts and solvates thereof, wherein n is 2, and $R^1$, $R^2$, $R^{3a}$ and $R^{3b}$ are as defined above in connection with Formula I.

In another embodiment, Compounds of the Invention are compounds represented by Formula I, and the pharmaceutically acceptable salts and solvates thereof, wherein $R^1$ is selected from the group consisting 2-furyl, 3-furyl, thien-2-yl, thien-3-yl, oxazol-2-yl, oxazol-4-yl, oxazol-5-yl, thiazol-2-yl, thiazol-4-yl, thiazol-5-yl, 1H-pyrazol-3-yl, 1H-pyrazol-4-yl, 1H-pyrazol-5-yl, isoxazol-3-yl, isoxazol-4-yl, isoxazol-5-yl, isothiazol-3-yl, isothiazol-4-yl, isothiazol-5-yl, 1,2,3 oxadiazol-4-yl, 1,2,3-oxadiazol-5-yl, 1,2,3-thiadiazol-4-yl, 1,2,3-thiadiazol-5-yl, 1,2,3 triazol-4-yl, 1,2,3-triazol-5-yl, 1,3,4-oxadiazolyl, and 1,3,4-thiadiazolyl, any of which is optionally substituted, and $R^2$, $R^{3a}$, $R^{3b}$, and n are as defined above in connection with Formula I.

In another embodiment, Compounds of the Invention are compounds represented by Formula I, and the pharmaceutically acceptable salts and solvates thereof, wherein $R^1$ is selected from the group consisting of optionally substituted thiazol-2-yl and optionally substituted 1,3,4-thiadiazolyl, and $R^2$, $R^{3a}$, $R^{3b}$, and n are as defined above in connection with Formula I.

In another embodiment, Compounds of the Invention are compounds represented by Formula I, and the pharmaceutically acceptable salts and solvates thereof, wherein $R^1$ is optionally substituted thiazol-2-yl, and $R^2$, $R^{3a}$, $R^{3b}$, and n are as defined above in connection with Formula I.

In another embodiment, Compounds of the Invention are compounds represented by Formula I, and the pharmaceutically acceptable salts and solvates thereof, wherein $R^1$ is thiazol-2-yl, and $R^2$, $R^{3a}$, $R^{3b}$, and n are as defined above in connection with Formula I.

In another embodiment, Compounds of the Invention are compounds represented by Formula I, and the pharmaceutically acceptable salts and solvates thereof, wherein $R^2$ is:

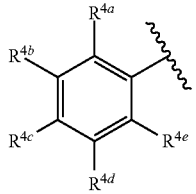

and $R^1$, $R^{3a}$, $R^{3b}$, and n are as defined above in connection with Formula I.

In another embodiment, Compounds of the Invention are compounds represented by Formula I, and the pharmaceutically acceptable salts and solvates thereof, wherein $R^2$ is:

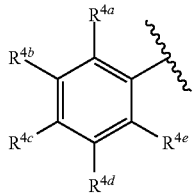

$R^{4c}$ is heteroaryloxy; $R^{4a}$, $R^{4b}$, $R^{4d}$, and $R^{4e}$ are each independently selected from the group consisting of hydrogen and halo, and $R^1$, $R^{3a}$, $R^{3b}$, and n are as defined above in connection with Formula I.

In another embodiment, Compounds of the Invention are compounds represented by Formula I, and the pharmaceutically acceptable salts and solvates thereof, wherein $R^2$ is:

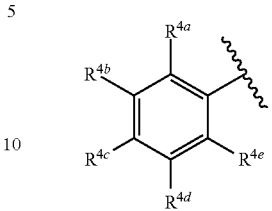

$R^{4c}$ is aryloxy; $R^{4a}$, $R^{4b}$, $R^{4d}$ and $R^{4e}$ are each independently selected from the group consisting of hydrogen and halo, and $R^1$, $R^{3a}$, $R^{3b}$, and n are as defined above in connection with Formula I.

In another embodiment, Compounds of the Invention are compounds represented by Formula I, and the pharmaceutically acceptable salts and solvates thereof, wherein $R^2$ is:

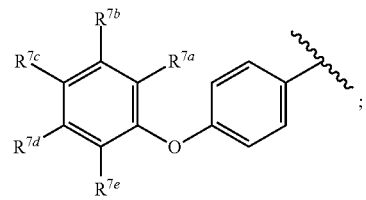

and
$R^{7a}$, $R^{7b}$, $R^{7c}$, $R^{7d}$, and $R^{7e}$ are each independently selected from the group consisting of hydrogen, alkyl, halo, nitro, cyano, hydroxy, amino, alkylamino, dialkylamino, haloalkyl, monohydroxyalkyl, dihydroxyalkyl, alkoxy, haloalkoxy, carboxy, and alkoxycarbonyl, and $R^1$, $R^{3a}$, $R^{3b}$, and n are as defined above in connection with Formula I.

In another embodiment, Compounds of the Invention are compounds represented by Formula I, and the pharmaceutically acceptable salts and solvates thereof, wherein $R^2$ is:

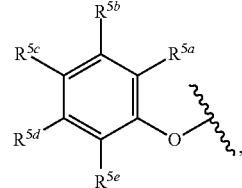

and $R^1$, $R^{3a}$, $R^{3b}$, $R^{5a}$, $R^{5b}$, $R^{5c}$, $R^{5d}$, $R^{5e}$ and n are as defined above in connection with Formula I.

In another embodiment, Compounds of the Invention are compounds represented by Formula I, and the pharmaceutically acceptable salts and solvates thereof, wherein $R^2$ is:

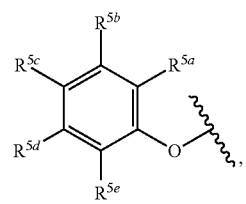

and $R^{5b}$, $R^{5c}$, $R^{5d}$, and $R^{5e}$ are each independently selected from the group consisting of hydrogen, alkyl, halo, cyano, hydroxy, alkoxy, and haloalkoxy, and $R^1$, $R^{3a}$, $R^{3b}$, and n are as defined above in connection with Formula I.

In another embodiment, Compounds of the Invention are compounds represented by Formula I, and the pharmaceutically acceptable salts and solvates thereof, wherein $R^2$ is:

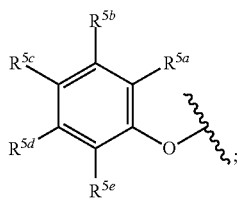

$R^{5b}$, $R^{5c}$, $R^{5d}$, and $R^{5e}$ are each independently selected from the group consisting of hydrogen, alkyl, halo, cyano, hydroxy, alkoxy, and haloalkoxy; and $R^{5a}$ is optionally substituted phenyl, and $R^1$, $R^{3a}$, $R^{3b}$, and n are as defined above in connection with Formula I.

In another embodiment, Compounds of the Invention are compounds represented by Formula I, and the pharmaceutically acceptable salts and solvates thereof, wherein $R^2$ is:

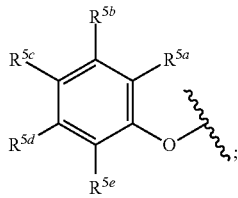

$R^{5b}$, $R^{5c}$, $R^{5d}$, and $R^{5e}$ are each independently selected from the group consisting of hydrogen, alkyl, halo, cyano, hydroxy, alkoxy, and haloalkoxy; and $R^{5a}$ is optionally substituted heteroaryl, and $R^1$, $R^{3a}$, $R^{3b}$, and n are as defined above in connection with Formula I.

In another embodiment, Compounds of the Invention are compounds represented by Formula I, and the pharmaceutically acceptable salts and solvates thereof, wherein $R^2$ is:

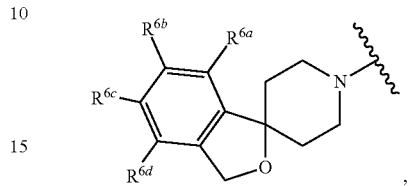

and $R^1$, $R^{3a}$, $R^{3b}$, $R^{6a}$, $R^{6b}$, $R^{6c}$, $R^{6d}$ and n are as defined above in connection with Formula I.

In another embodiment, Compounds of the Invention are compounds represented by Formula I, and the pharmaceutically acceptable salts and solvates thereof, wherein $R^2$ is:

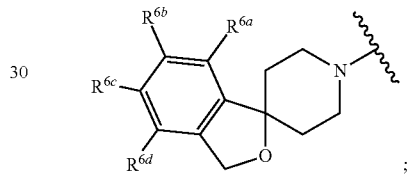

and $R^{6a}$, $R^{6b}$, $R^{6c}$, and $R^{6d}$ are each hydrogen, and $R^1$, $R^{3a}$, $R^{3b}$, and n are as defined above in connection with Formula I.

In another embodiment, Compounds of the Invention are compounds of TABLE 2, and the pharmaceutically acceptable salts and solvates thereof.

TABLE 2

| Compound Example No. | Structure |
| --- | --- |
| 1 | ![structure] |

TABLE 2-continued

| Compound Example No. | Structure |
|---|---|
| 2 | 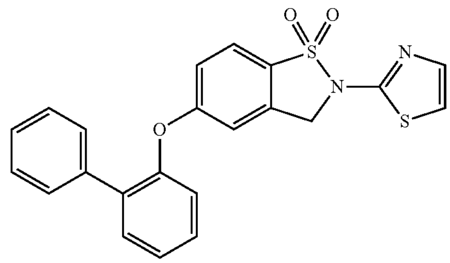 [SMILES: O=S1(=O)c2ccc(Oc3ccccc3-c3ccccc3)cc2CN1c1nccs1] |
| 3 | 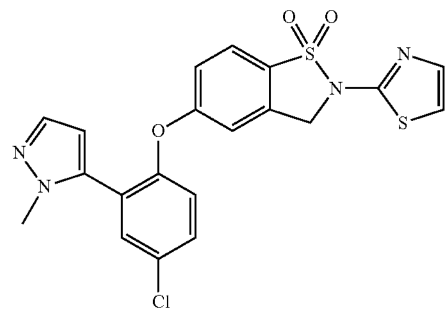 [SMILES: Cn1nccc1-c1cc(Cl)ccc1Oc1ccc2c(c1)CN(c1nccs1)S2(=O)=O] |
| 4 | 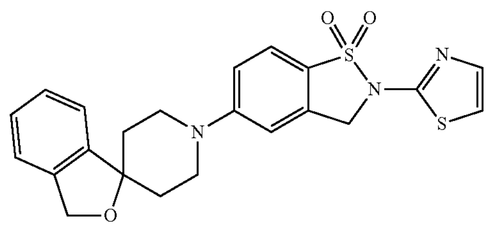 [SMILES: O=S1(=O)c2ccc(N3CCC4(CC3)OCc3ccccc34)cc2CN1c1nccs1] |
| 5 | 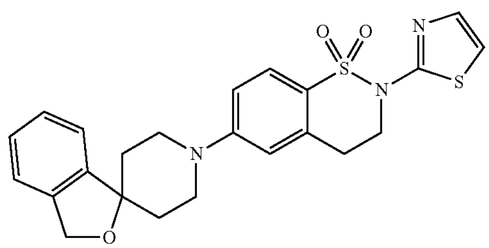 [SMILES: O=S1(=O)c2ccc(N3CCC4(CC3)OCc3ccccc34)cc2CCN1c1nccs1] |
| 6 | 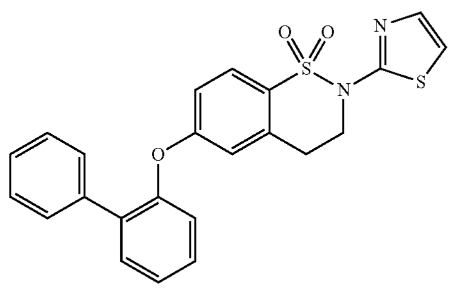 [SMILES: O=S1(=O)c2ccc(Oc3ccccc3-c3ccccc3)cc2CCN1c1nccs1] |
| 7 | 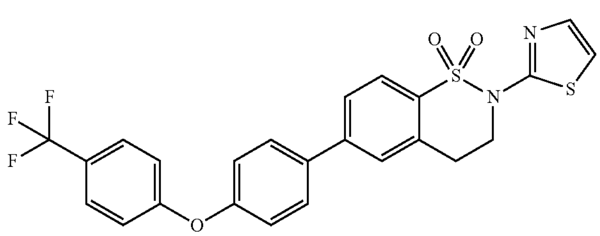 [SMILES: O=S1(=O)c2ccc(-c3ccc(Oc4ccc(C(F)(F)F)cc4)cc3)cc2CCN1c1nccs1] |

The chemical names of the compound examples are provided in TABLE 3.

TABLE 3

| Compound Example No. | Chemical Name |
|---|---|
| 1 | 5-(2-(pyridazin-4-yl)-4-(trifluoromethyl)phenoxy)-2-(thiazol-2-yl)-2,3-dihydrobenzo[d]isothiazole 1,1-dioxide |
| 2 | 5-([1,1'-biphenyl]-2-yloxy)-2-(thiazol-2-yl)-2,3-dihydrobenzo[d]isothiazole 1,1-dioxide |
| 3 | 5-(4-chloro-2-(1-methyl-1H-pyrazol-5-yl)phenoxy)-2-(thiazol-2-yl)-2,3-dihydrobenzo[d]isothiazole 1,1-dioxide |
| 4 | 5-(3H-spiro[isobenzofuran-1,4'-piperidin]-1'-yl)-2-(thiazol-2-yl)-2,3-dihydrobenzo[d]isothiazole 1,1-dioxide |
| 5 | 6-(3H-spiro[isobenzofuran-1,4'-piperidin]-1'-yl)-2-(thiazol-2-yl)-3,4-dihydro-2H-benzo[e][1,2]thiazine 1,1-dioxide |
| 6 | 6-([1,1'-biphenyl]-2-yloxy)-2-(thiazol-2-yl)-3,4-dihydro-2H-benzo[e][1,2]thiazine 1,1-dioxide |
| 7 | 2-(thiazol-2-yl)-6-(4-(4-(trifluoromethyl)phenoxy)phenyl)-3,4-dihydro-2H-benzo[e][1,2]thiazine 1,1-dioxide |

In another embodiment, the present disclosure provides a pharmaceutical composition comprising a Compound of the Invention and a pharmaceutically acceptable carrier.

In another embodiment, the present disclosure provides a method of treating a disorder responsive to the blockade of sodium channels in a mammal suffering from said disorder, comprising administering to a mammal in need of such treatment an effective amount of a Compound of the Invention.

In another embodiment, the present disclosure provides a method of treating a disorder responsive to the blockade of TTX-resistant sodium channels in a mammal suffering from said disorder, comprising administering to a mammal in need of such treatment an effective amount of a Compound of the Invention.

In another embodiment, the present disclosure provides a method of treating a disorder responsive to the blockade of TTX-sensitive sodium channels in a mammal suffering from said disorder, comprising administering to a mammal in need of such treatment an effective amount of a Compound of the Invention.

In another embodiment, the present disclosure provides a method of treating a disorder responsive to the blockade of $Na_v1.7$ sodium channels in a mammal suffering from said disorder, comprising administering to a mammal in need of such treatment an effective amount of a Compound of the Invention.

In another embodiment, the present disclosure provides a method of treating stroke, neuronal damage resulting from head trauma, epilepsy, seizures, neuronal loss following global and focal ischemia, pain, migraine, primary erythromelalgia, paroxysmal extreme pain disorder, cerebellar atrophy, ataxia, mental retardation, a neurodegenerative disorder, manic depression, tinnitus, myotonia, a movement disorder, or cardiac arrhythmia, or providing local anesthesia in a mammal, comprising administering to a mammal in need of such treatment an effective amount of a Compound of the Invention.

In another embodiment, the present disclosure provides a method for treating pain, comprising administering to a mammal in need of such treatment an effective amount of a Compound of the Invention.

In another embodiment, the present disclosure provides a method for the preemptive or palliative treatment of pain, comprising administering to a mammal in need of such treatment an effective amount of a Compound of the Invention.

In another embodiment, the present disclosure provides a method of treating chronic pain, inflammatory pain, neuropathic pain, acute pain, and surgical pain, comprising administering to a mammal in need of such treatment an effective amount of a Compound of the Invention.

In another embodiment, the present disclosure provides a method of modulating sodium channels, e.g., $Na_v1.7$ sodium channels, in a mammal, comprising administering to the mammal in need of such modulation at least one Compound of the Invention.

In another embodiment, the present disclosure provides a pharmaceutical composition, comprising a Compound of the Invention useful for treating a disorder responsive to the blockade of sodium ion channels such as pain.

In another embodiment, the present disclosure provides a Compound of the Invention for use in treating a disorder responsive to the blockade of sodium ion channels such as pain.

In another embodiment, the present disclosure provides a Compound of the Invention wherein said compound is $^3H$, $^{11}C$, or $^{14}C$ radiolabeled.

In another embodiment, the present disclosure provides a method of screening a candidate compound for the ability to bind to a binding site on a protein using a radiolabeled Compound of the Invention, comprising:

a) introducing a fixed concentration of said radiolabeled compound to an in vitro preparation comprising a soluble or membrane-associated sodium channel, subunit or fragment thereof under conditions that permit said radiolabeled compound to bind to said channel, subunit or fragment, respectively, to form a conjugate;

b) titrating said conjugate with said candidate compound; and c) determining the ability of said candidate compound to displace said radiolabeled Compound of the Invention from said channel, subunit or fragment.

In another embodiment, the present disclosure provides a method of preparing a pharmaceutical composition, comprising admixing a therapeutically effective amount of a Compound of the Invention with a pharmaceutically acceptable carrier.

In another embodiment, the present disclosure provides the use of a Compound of the Invention in the manufacture of a medicament for treating or preventing stroke, neuronal damage resulting from head trauma, epilepsy, seizures, neuronal loss following global and focal ischemia, pain, migraine, primary erythromelalgia, paroxysmal extreme pain disorder, cerebellar atrophy, ataxia, mental retardation, a neurodegenerative disorder, manic depression, tinnitus, myotonia, a movement disorder, or cardiac arrhythmia, or providing local anesthesia.

In another embodiment, the present disclosure provides the use of a Compound of the Invention in the manufacture of a medicament for treating pain.

In another embodiment, the present disclosure provides a Compound of the Invention for use in the treatment or prevention of stroke, neuronal damage resulting from head trauma, epilepsy, seizures, neuronal loss following global and focal ischemia, pain, migraine, primary erythromelalgia, paroxysmal extreme pain disorder, cerebellar atrophy, ataxia, mental retardation, a neurodegenerative disorder, manic depression, tinnitus, myotonia, a movement disorder, or cardiac arrhythmia, or providing local anesthesia.

In another embodiment, the present disclosure provides a Compound of the Invention for use in the treatment or prevention of pain.

For the purpose of the present disclosure, the term "alkyl" as used by itself or as part of another group refers to a straight- or branched-chain aliphatic hydrocarbon containing 1, 2, 3, 4, 5, 6, 7, 8, 9, 10, 11, or 12 carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{3-10}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a branched chain $C_{1-4}$ alkyl group. In another embodiment, the alkyl group is chosen from a straight or branched chain $C_{3-6}$ alkyl group. In another embodiment, the alkyl group is chosen from a straight or branched chain $C_{2-4}$ alkyl group. Non-limiting exemplary $C_{1-10}$ alkyl groups include methyl, ethyl, n-propyl, n-butyl, n-pentyl, n-hexyl, n-heptyl, n-octyl, n-nonyl, and n-decyl, isopropyl, sec-butyl, tert-butyl, iso-butyl, iso-pentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryl oxy, aralkyloxy, alkylthio, sulfonamido, alkylcarbonyl, aryl carbonyl, alkylsulfonyl, arylsulfonyl, ureido, guanidino, and cycloalkyl. In one embodiment, the optionally substituted alkyl is substituted with two substituents. In another embodiment, the optionally substituted alkyl is substituted with one substituent. Non-limiting exemplary optionally substituted alkyl groups include —$CH_2CH_2NO_2$, —$CH_2CH_2CO_2H$, —$CH_2CH_2SO_2CH_3$, —$CH_2CH_2COPh$, and —$CH_2C_6H_{11}$.

For the purpose of the present disclosure, the term "cycloalkyl" as used by itself or as part of another group refers to saturated and partially unsaturated (containing e.g. one or two double bonds) cyclic aliphatic hydrocarbons containing one, two or three rings having 3, 4, 5, 6, 7, 8, 9, 10, 11, or 12 carbon atoms (i.e., $C_{3-12}$ cycloalkyl) or the number of carbons designated. In one embodiment, the cycloalkyl group has two rings. In another embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, cyclononyl, cyclodecyl, cycloundecyl, cyclododecyl, norbornyl, decalin, adamantyl, cyclopropenyl, cyclobutenyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclononatrienyl, cyclodecenyl, cyclodecadienyl, cyclotetradecenyl, and cyclododecadienyl.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkyl is substituted with two substituents. In another embodiment, the optionally substituted cycloalkyl is substituted with one substituent. Non-limiting exemplary optionally substituted cycloalkyl groups include:

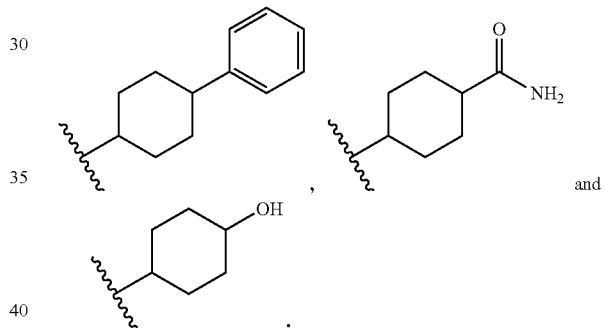

For the purpose of the present disclosure, the term "alkenyl" as used by itself or as part of another group refers to an alkyl group having 2, 3, 4, 5, 6, 7, 8, 9, or 10 carbon atoms ($C_{2-10}$alkenyl) and including at least one, e.g. one, two or three, carbon-carbon double bond. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, iso-butylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl, and the like.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group having 2, 3, 4, 5, 6, 7, 8, 9, or 10 carbon atoms (($C_{2-10}$)alkynyl) and including at least one, e.g. one, two or three, carbon-carbon triple bond. In one embodiment, the alkynyl has one carbon-to-carbon triple bond. In another embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, aryl sulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "monohydroxyalkyl" as used by itself or as part of another group refers to an alkyl group as defined above substituted with exactly one hydroxy group. Non-limiting exemplary monohydroxyalkyl groups include hydroxymethyl, hydroxyethyl, hydroxypropyl and hydroxybutyl groups. In one embodiment, the monohydroxyalkyl group is a $C_{1-6}$ monohydroxyalkyl. In another embodiment, the monohydroxyalkyl group is a $C_{1-4}$ monohydroxyalkyl.

For the purpose of the present disclosure, the term "dihydroxyalkyl" as used by itself or as part of another group refers to an alkyl group as defined above substituted with exactly two hydroxy groups. Non-limiting exemplary dihydroxyalkyl groups include 1,2-dihydroxyethyl and 1,3-dihydroxyprop-2-yl. In one embodiment, the dihydroxyalkyl group is a $C_{2-6}$ dihydroxyalkyl. In another embodiment, the dihydroxyalkyl group is a $C_{2-4}$ dihydroxyalkyl. In another embodiment, the dihydroxyalkyl group is a $C_2$ dihydroxyalkyl.

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-6}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —$SCH_3$, and —$SCH_2CH_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "heteroalkyl" as used by itself or part of another group refers to a stable straight or branched chain hydrocarbon radical containing 1, 2, 3, 4, 5, 6, 7, 8, 9, or 10 carbon atoms and 1 or 2 heteroatoms, which can be the same or different, selected from O, N, or S, wherein: 1) the nitrogen atom(s) and sulfur atom(s) can optionally be oxidized (to yield an N-oxide, sulfoxide or sulfone); and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. Non-limiting exemplary heteroalkyl groups include —$CH_2OCH_2CH_2OCH_3$, —$OCH_2CH_2OCH_2CH_2OCH_3$, —$CH_2NHCH_2CH_2OCH_2$, —$OCH_2CH_2NH_2$, and —$NHCH_2CH_2N(H)CH_3$.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, trichloromethoxy, and 2,2,2-trifluoroethoxy.

For the purpose of the present disclosure, the term "aryl" as used by itself or as part of another group refers to a monocyclic or bicyclic aromatic ring system having from six to fourteen carbon atoms (i.e., $C_{6-14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

For the purpose of the present disclosure, the term "optionally substituted aryl" as used herein by itself or as part of another group means that the aryl as defined above is either unsubstituted or substituted with 1, 2, 3, 4, or 5 substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, or (heteroaryl)alkyl. In one embodiment, the optionally substituted aryl is an optionally substituted phenyl. In another embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 2-cyanophenyl, 3-methylphenyl, 3-methoxyphenyl, 3-fluorophenyl, 3-chlorophenyl, 3-cyanophenyl, 4-methylphenyl, 4-ethylphenyl, 4-methoxyphenyl, 4-fluorophenyl, 4-chlorophenyl, 4-cyanophenyl, 2,6-difluorophenyl, 2,6-di-chlorophenyl, 2-methyl, 3-methoxyphenyl, 2-ethyl, 3-methoxyphenyl, 3,4-dimethoxyphenyl, 3,5-di-fluorophenyl 3,5-di-methylphenyl, 3,5-dimethoxy, 4-methylphenyl, 2-fluoro-3-chlorophenyl, 2-trifluoromethyl-4-cyanophenyl, 2-fluoro-5-chlorophenyl, 2-fluoro-5-chlorophenyl, 2-fluoro-4-chlorophenyl, 2-cyano-3-trifluorophenyl and 3-chloro-4-fluorophenyl. The term optionally substituted aryl is meant to include groups having fused optionally substituted cycloalkyl and fused optionally substituted heterocyclo rings. Examples include:

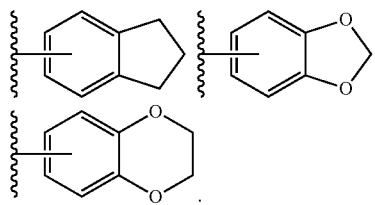

For the purpose of the present disclosure, the term "aryloxy" as used by itself or as part of another group refers to an optionally substituted aryl attached to a terminal oxygen atom. Non-limiting exemplary aryloxy groups include:

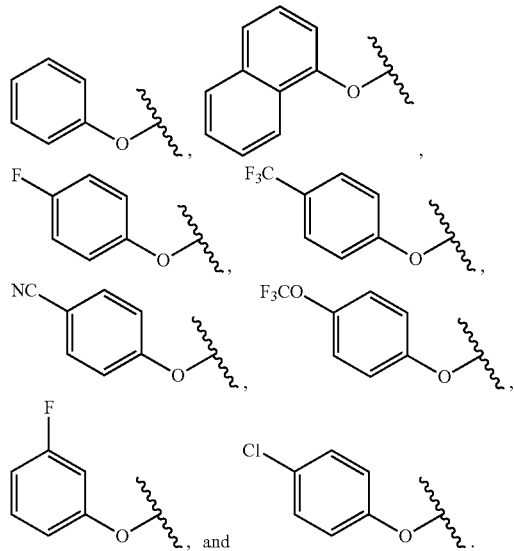

For the purpose of the present disclosure, the term "heteroaryloxy" as used by itself or as part of another group refers to an optionally substituted heteroaryl attached to a terminal oxygen atom. Non-limiting exemplary heteroaryloxy groups include:

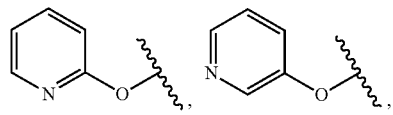

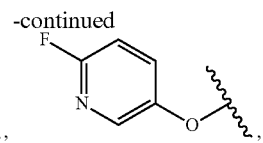

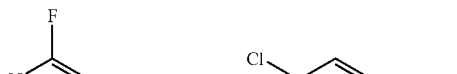

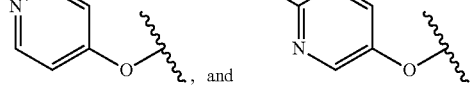

For the purpose of the present disclosure, the term "aralkyloxy" as used by itself or as part of another group refers to an aralkyl group attached to a terminal oxygen atom. A non-limiting exemplary aralkyloxy group is benzyloxy ($PhCH_2O—$).

For the purpose of the present disclosure, the term "heteroaryl" or "heteroaromatic" refers to monocyclic and bicyclic aromatic ring systems having 5, 6, 7, 8, 9, 10, 11, 12, 13, or 14 ring atoms (i.e., $C_{5-14}$ heteroaryl or 5- to 14-membered heteroaryl) and 1, 2, 3, or 4 heteroatoms independently chosen from oxygen, nitrogen and sulfur. In one embodiment, the heteroaryl has three heteroatoms. In another embodiment, the heteroaryl has two heteroatoms. In another embodiment, the heteroaryl has one heteroatom. In another embodiment, the heteroaryl is a $C_5$ heteroaryl. In another embodiment, the heteroaryl is a $C_6$ heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In another embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Non-limiting exemplary N-oxides include pyridyl N-oxide.

For the purpose of the present disclosure, the term "optionally substituted heteroaryl" as used by itself or as part of another group means that the heteroaryl as defined above is either unsubstituted or substituted with 1, 2, 3, or 4 substituents, e.g., one or two substituents, independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted heteroaryl has one substituent. In another embodiment, the optionally substituted heteroaryl is an optionally substituted pyridyl, i.e., 2-, 3-, or 4-pyridyl. Any available carbon or nitrogen atom can be substituted. In another embodiment, the optionally substituted heteroaryl is an optionally substituted indole.

For the purpose of the present disclosure, the term "heterocyclo" as used by itself or as part of another group refers to saturated and partially unsaturated (e.g., containing one or two double bonds) cyclic groups containing 1, 2, or 3 rings having from 2, 3, 4, 5, 6, 7, 8, 9, 10, 11, 12, 13, or 14 carbon atoms (i.e., $C_{2-14}$ heterocyclo) and one or two oxygen, sulfur and/or nitrogen atoms. The term "heterocyclo" is meant to include cyclic ureido groups such as 2-imidazolidinone and cyclic amide groups such as β-lactam, γ-lactam, δ-lactam and ε-lactam. The term "heterocyclo" is also meant to include groups having fused optionally substituted aryl groups, e.g., indolinyl. In one embodiment, the heterocyclo group is chosen from a 5- or 6-membered cyclic group containing one ring and one or two oxygen and/or nitrogen atoms. The heterocyclo can be optionally linked to the rest of the molecule through a carbon or nitrogen atom. In another embodiment the "heterocyclo" is a 3- to 8-membered heterocyclo. Non-limiting exemplary heterocyclo, i.e. 3- to 8-membered heterocyclo, groups include 2-imidazolidinone, piperidinyl, morpholinyl, piperazinyl, pyrrolidinyl, and indolinyl.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. Substitution may occur on any available carbon or nitrogen atom. Non-limiting exemplary optionally substituted heterocyclo groups include:

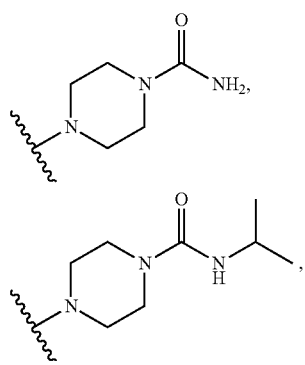

For the purpose of the present disclosure, the term "amino" as used by itself or as part of another group refers to —$NH_2$.

For the purpose of the present disclosure, the term "alkylamino" as used by itself or as part of another group refers to —$NHR^{13}$, wherein $R^{13}$ is alkyl.

For the purpose of the present disclosure, the term "dialkylamino" as used by itself or as part of another group refers to —$NR^{14a}R^{14b}$, wherein $R^{14a}$ and $R^{14b}$ are each independently alkyl or $R^{14a}$ and $R^{14b}$ are taken together to form a 3- to 8-membered optionally substituted heterocyclo.

For the purpose of the present disclosure, the term "hydroxyalkylamino" as used by itself or as part of another group refers to —$NHR^{15}$, wherein $R^{15}$ is monohydroxyalkyl or dihydroxyalkyl.

For the purpose of the present disclosure, the term "arylamino" as used by itself or as part of another group refers to —NR$^{16a}$R$^{16b}$, wherein R$^{16a}$ is optionally substituted aryl and R$^{16b}$ is hydrogen or alkyl.

For the purpose of the present disclosure, the term "cycloalkylamino" as used by itself or as part of another group refers to —NR$^{17a}$R$^{17b}$, wherein R$^{17a}$ is optionally substituted cycloalkyl and R$^{17b}$ is hydrogen or alkyl.

For the purpose of the present disclosure, the term "heteroarylamino" as used by itself or as part of another group refers to —NR$^{18a}$R$^{18b}$ wherein R$^{18a}$ is optionally substituted heteroaryl and R$^{18b}$ is hydrogen or alkyl.

For the purpose of the present disclosure, the term "heterocycloamino" as used by itself or as part of another group refers to —NR$^{19a}$R$^{19b}$ wherein R$^{19a}$ is optionally substituted heterocyclo and R$^{19b}$ is hydrogen or alkyl.

For the purpose of the present disclosure, the term "(amino)alkyl" as used by itself or as part of another group refers to an alkyl group substituted with an amino group. Non-limiting exemplary amino alkyl groups include —CH$_2$CH$_2$NH$_2$, —CH$_2$CH$_2$CH$_2$NH$_2$, and —CH$_2$CH$_2$CH$_2$CH$_2$NH$_2$.

For the purpose of the present disclosure, the term "diaminoalkyl" as used by itself or as part of another group refers an alkyl group substituted with two amino groups. A non-limiting exemplary diaminoalkyl includes —CH$_2$CH(NH$_2$)CH$_2$CH$_2$NH$_2$.

For the purpose of the present disclosure, the term "(alkylamino)alkyl" as used by itself or as part of another group refers an alkyl group substituted with an alkylamino group. A non-limiting exemplary (alkylamino)alkyl group is —CH$_2$CH$_2$N(H)CH$_3$.

For the purpose of the present disclosure, the term "(dialkylamino)alkyl" as used by itself or as part of another group refers to an alkyl group substituted by a dialkylamino group. A non-limiting exemplary (dialkylamino)alkyl group is —CH$_2$CH$_2$N(CH$_3$)$_2$.

For the purpose of the present disclosure, the term "(cyano)alkyl" as used by itself or as part of another group refers to an alkyl group substituted with one or more cyano, e.g., —CN, groups. Non-limiting exemplary (cyano)alkyl groups include —CH$_2$CH$_2$CN, —CH$_2$CH$_2$CH$_2$CN, and —CH$_2$CH$_2$CH$_2$CH$_2$CN.

For the purpose of the present disclosure, the term "carboxamido" as used by itself or as part of another group refers to a radical of formula —C(=O)NR$^{20a}$R$^{20b}$, wherein R$^{20a}$ and R$^{20b}$ are each independently hydrogen, optionally substituted alkyl, optionally substituted aryl, or optionally substituted heteroaryl, or R$^{20a}$ and R$^{20b}$ taken together with the nitrogen atom to which they are attached from a 3- to 8-membered heterocyclo group. In one embodiment, R$^{20a}$ and R$^{20b}$ are each independently hydrogen or optionally substituted alkyl. Non-limiting exemplary carboxamido groups include —CONH$_2$, —CON(H)CH$_3$, CON(CH$_3$)$_2$, and CON(H)Ph.

For the purpose of the present disclosure, the term "(carboxamido)alkyl" as used by itself or as part of another group refers to an alkyl group substituted with a carboxamido group. Non-limiting exemplary (carboxamido)alkyl groups include —CH$_2$CONH$_2$, —C(H)CH$_3$—CONH$_2$, and —CH$_2$CON(H)CH$_3$.

For the purpose of the present disclosure, the term "sulfonamido" as used by itself or as part of another group refers to a radical of the formula —SO$_2$NR$^{21a}$R$^{21b}$, wherein R$^{21a}$ and R$^{21b}$ are each independently hydrogen, optionally substituted alkyl, or optionally substituted aryl, or R$^{21a}$ and R$^{21b}$ taken together with the nitrogen atom to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

For the purpose of the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

For the purpose of the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

For the purpose of the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

For the purpose of the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "halo" or "halogen" as used by itself or as part of another group refers to —F, —Cl, Br, or —I.

For the purpose of the present disclosure, the term "nitro" as used by itself or as part of another group refers to a radical of the formula —NO$_2$.

For the purpose of the present disclosure, the term "cyano" as used by itself or as part of another group refers to a radical of the formula —CN.

For the purpose of the present disclosure, the term "hydroxy" as used by itself or as part of another group refers to a radical of the formula —OH.

For the purpose of the present disclosure, the term "carboxyalkyl" as used by itself or as part of another group refers to any of the above-mentioned alkyl groups substituted with a —COOH. Non-limiting exemplary carboxyalkyl groups include —CH$_2$CO$_2$H and —CH(CH$_3$)—CO$_2$H.

For the purpose of the present disclosure, the term "alkoxycarbonyl" as used by itself or as part of another group refers to a carbonyl group, i.e., —C(=O)—, substituted by an alkoxy group. Non-limiting exemplary alkoxycarbonyl groups are —CO$_2$Me and —CO$_2$Et.

For the purpose of the present disclosure, the term "(alkoxycarbonyl)alkyl" as used by itself or as part of another group refers to an alkyl group substituted with an alkoxycarbonyl group. Non-limiting exemplary (alkoxycarbonyl)alkyl groups include —CH$_2$CO$_2$CH$_3$ and —C(H)CH$_3$—CO$_2$CH$_3$.

For the purpose of the present disclosure, the term "aralkyl" as used by itself or as part of another group refers to an alkyl group substituted with one, two, or three optionally substituted aryl groups. In one embodiment, the aralkyl group is a C$_{1-4}$ alkyl substituted with one optionally substituted aryl group. Non-limiting exemplary aralkyl groups include benzyl, phenethyl, —CHPh$_2$, and —CH(4-F-Ph)$_2$.

For the purpose of the present disclosure, the term "ureido" as used by itself or as part of another group refers to a radical of the formula —NR$^{22a}$—C(=O)—NR$^{22b}$R$^{22c}$, wherein $R^{22a}$ is hydrogen, alkyl, or optionally substituted aryl, and $R^{22b}$ and $R^{22c}$ are each independently hydrogen, alkyl, or optionally substituted aryl, or $R^{22b}$ and $R^{22c}$ taken together with the nitrogen to which they are attached form a 4- to 8-membered heterocyclo group. Non-limiting exemplary ureido groups include —NH—C(C=O)—NH$_2$ and —NH—C(C=O)—NHCH$_3$.

For the purpose of the present disclosure, the term "guanidino" as used by itself or as part of another group refers to a radical of the formula —NR$^{23a}$—C(=NR$^{24}$)—NR$^{23b}$R$^{23c}$ wherein $R^{23a}$, $R^{23b}$, and $R^{23c}$ are each independently hydrogen, alkyl, or optionally substituted aryl, and $R^{24}$ is hydrogen, alkyl, cyano, alkylsulfonyl, alkylcarbonyl, carboxamido, or sulfonamido. Non-limiting exemplary guanidino groups include —NH—C(C=NH)—NH$_2$, —NH—C(C=NCN)—NH$_2$, —NH—C(C=NH)—NHCH$_3$.

For the purpose of the present disclosure, the term "azido" as used by itself or as part of another group refers to a radical of the formula —N$_3$.

For the purpose of the present disclosure, the term "(heterocyclo)alkyl" as used by itself or as part of another group refers to an alkyl group substituted with one, two, or three optionally substituted heterocyclo groups. In one embodiment, the (heterocyclo)alkyl is a C$_{1-4}$ alkyl substituted with one optionally substituted heterocyclo group. Non-limiting exemplary (heterocyclo)alkyl groups include:

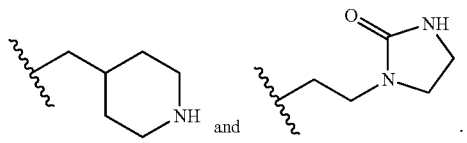 [SMILES: *CC1CCNCC1 ; *CCN1CCNC1=O]

For the purpose of the present disclosure, the term "(heteroaryl)alkyl" as used by itself or as part of another group refers to an alkyl group substituted with one, two, or three optionally substituted heteroaryl groups. In one embodiment, the (heteroaryl)alkyl group is a C$_{1-4}$ alkyl substituted with one optionally substituted heteroaryl group. Non-limiting exemplary (heteroaryl)alkyl groups include:

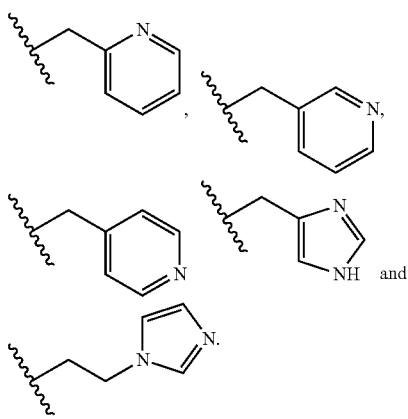

For the purpose of the present disclosure, the term "alkylcarbonylamino" as used by itself or as part of another group refers to an alkylcarbonyl group attached to an amino. A non-limiting exemplary alkylcarbonylamino group is —NHCOCH$_3$.

For the purpose of the present disclosure, the term "alkylcarbonyloxy" as used by itself or as part of another group refers to oxygen substituted by one of the above-mentioned alkylcarbonyl groups. A non-limiting exemplary alkylcarbonyloxy group is —OCOCH$_3$.

The present disclosure encompasses any of the Compounds of the Invention being isotopically-labeled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^{2}$H, $^{3}$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, e.g., $^{3}$H, $^{11}$C, and $^{14}$C. Isotopically-labeled Compounds of the Invention can be prepared by methods known in the art.

The present disclosure encompasses $^{3}$H, $^{11}$C, or $^{14}$C radiolabeled Compounds of the Invention and the use of any such compounds as radioligands for their ability to bind to the sodium channel. For example, one use of the labeled compounds of the present disclosure is the characterization of specific receptor binding. Another use of a labeled Compound of the Invention is an alternative to animal testing for the evaluation of structure-activity relationships. For example, the receptor assay can be performed at a fixed concentration of a labeled Compound of the Invention and at increasing concentrations of a test compound in a competition assay. For example, a titrated Compound of the Invention can be prepared by introducing tritium into the particular compound, for example, by catalytic dehalogenation with tritium. This method may include reacting a suitably halogen-substituted precursor of the compound with tritium gas in the presence of a suitable catalyst, for example, Pd/C, in the presence or absence of a base. Other suitable methods for preparing titrated compounds can be found in Filer, *Isotopes in the Physical and Biomedical Sciences, Vol. 1, Labeled Compounds (Part A)*, Chapter 6 (1987). $^{14}$C-labeled compounds can be prepared by employing starting materials having a $^{14}$C carbon.

Some of the Compounds of the Invention may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both. E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treat," "treating" or "treatment" is meant to encompass administering to a subject a compound of the present disclosure for the purposes of amelioration or cure, including preemptive and palliative treatment.

The term "about," as used herein in connection with a measured quantity, refers to the normal variations in that measured quantity, as expected by the skilled artisan making the measurement and exercising a level of care commensurate with the objective of measurement and the precision of the measuring equipment.

The present disclosure encompasses Compounds of the Invention in salt form, including non-toxic pharmaceutically acceptable salts, and including their preparation and use. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular Compound of the Invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The present disclosure encompasses the preparation and use of solvates of Compounds of the Invention. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Invention can be present as solvated forms with a pharmaceutically acceptable solvent, such as water, methanol, ethanol, and the like, and it is intended that the disclosure includes both solvated and unsolvated forms of Compounds of the Invention. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1):Article 12 (2004), and A. L. Bingham et al., *Chem. Commun.* 603-604 (2001). A typical, non-limiting, process of preparing a solvate would involve dissolving a Compound of the Invention in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Since Compounds of the Invention are blockers of sodium ($Na^+$) channels, a number of diseases and conditions mediated by sodium ion influx can be treated by employing these compounds. The present disclosure is thus directed generally to a method of treating a disorder responsive to the blockade of sodium channels in a mammal suffering from, or at risk of suffering from, said disorder, said method comprising administering to the mammal an effective amount of one or more Compounds of the Invention.

The present disclosure is further directed to a method of modulating sodium channels in a mammal in need thereof, said method comprising administering to the mammal a modulating-effective amount of at least one Compound of the Invention.

More specifically, the present disclosure provides a method of treating stroke, neuronal damage resulting from head trauma, epilepsy, neuronal loss following global and focal ischemia, pain (e.g., acute pain, chronic pain, which includes but is not limited to neuropathic pain, postoperative pain, and inflammatory pain, or surgical pain), a neurodegenerative disorder (e.g., Alzheimer's disease, amyotrophic lateral sclerosis (ALS), or Parkinson's disease), migraine, manic depression, tinnitus, myotonia, a movement disorder, or cardiac arrhythmia, or providing local anesthesia in a mammal. In one embodiment, the disclosure provides a method of treating pain. In another embodiment, the type of pain is chronic pain. In another embodiment, the type of pain is neuropathic pain. In another embodiment, the type of pain is postoperative pain. In another embodiment, the type of pain is inflammatory pain. In another embodiment, the type of pain is surgical pain. In another embodiment, the type of pain is acute pain. In another embodiment, the treatment of pain (e.g., chronic pain, such as neuropathic pain, postoperative pain, or inflammatory pain, acute pain or surgical pain) is preemptive. In another embodiment, the treatment of pain is palliative. In each instance, such method of treatment requires administering to a mammal in need of such treatment an amount of a Compound of the Invention that is therapeutically effective in achieving said treatment. In one embodiment, the amount of such compound is the amount that is effective to block sodium channels in vitro. In another embodiment, the amount of such compound is the amount that is effective to block sodium channels in vivo.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 18:387-391 (2000)).

The inflammatory process is a complex series of biochemical and cellular events activated in response to tissue injury or the presence of foreign substances (Levine, *Inflammatory Pain, In: Textbook of Pain*, Wall and Melzack eds., 3rd ed., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, that associated with osteoarthritis and rheumatoid arthritis.

Chronic neuropathic pain is a heterogeneous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present disclosure is also directed to the use of a Compound of the Invention in the manufacture of a medicament for treating a disorder responsive to the blockade of sodium channels (e.g., any of the disorders listed above) in a mammal suffering from said disorder.

General Synthesis of Compounds

Compounds of the Invention can be prepared using methods known to those skilled in the art in view of this disclosure. For example, compounds having Formula I can be prepared according to Scheme 1. Briefly, compound A' or A" is converted to compound B by treatment with ClSO$_3$H or Cl$_2$, respectively. Compound B is treated with R$^1$—NH$_2$ to form the sulfonamide C. The ester of compound C is reduced to give compound D, and compound D is cyclized to give compound E. Compound E is reacted with the appropriate reagent (F, G, or H) to give a compound having Formula I-a, Formula I-b, Formula I-c.

Scheme 1

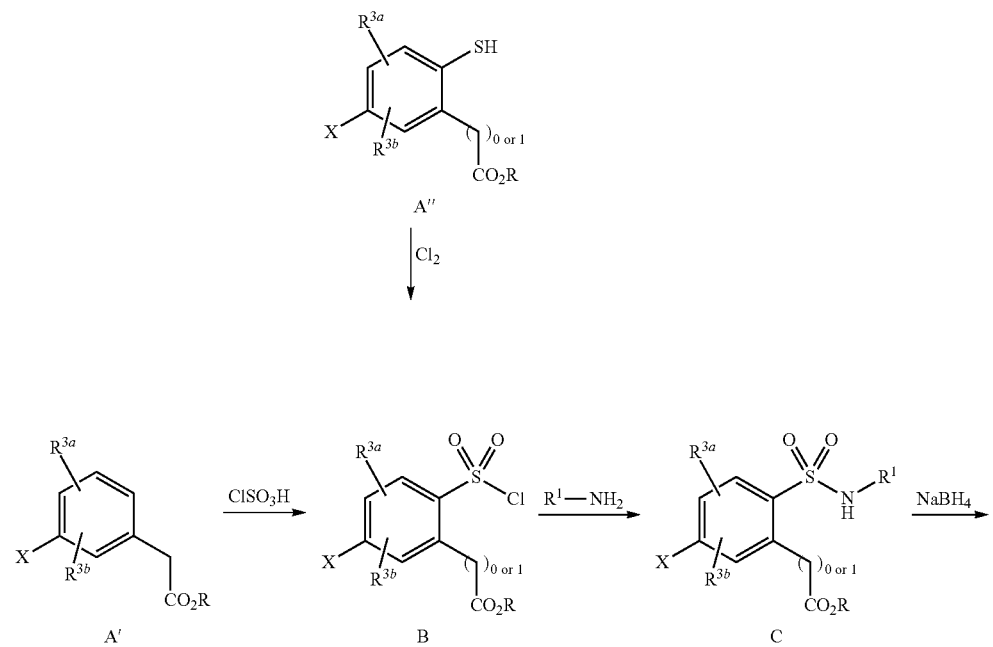

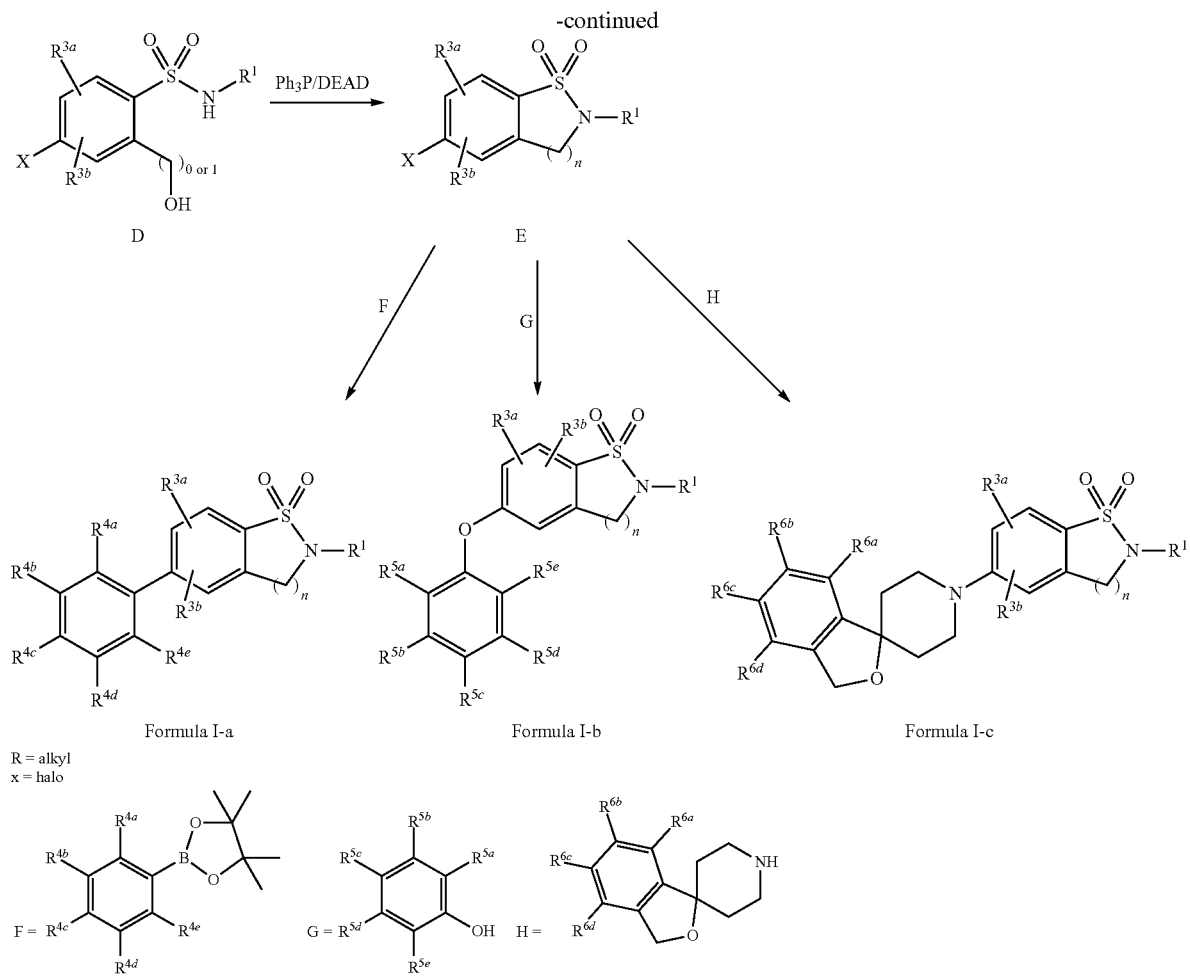

Testing of Compounds

Representative Compounds of the Invention were assessed by sodium mobilization and/or electrophysiological assays for sodium channel blocker activity. One aspect of the present disclosure is based on the use of the Compounds of the Invention as sodium channel blockers. Based upon this property, Compounds of the Invention are considered useful in treating a condition or disorder responsive to the blockade of sodium ion channels, e.g., stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, cardiac arrhythmia, or providing local anesthesia. Compounds of the Invention are also expected to be effective in treating pain, e.g., acute pain, chronic pain, which includes but is not limited to, neuropathic pain, postoperative pain, and inflammatory pain, or surgical pain.

More specifically, the present disclosure is directed to Compounds of the Invention that are blockers of sodium channels. According to the present disclosure, those compounds having useful sodium channel blocking properties exhibit an $IC_{50}$ for $Na_v1.1$, $Na_v1.2$, $Na_v1.3$, $Na_v1.4$, $Na_v1.5$, $Na_v1.6$, $Na_v1.7$, $Na_v1.8$, and/or $Na_v1.9$ of about 100 μM or less, e.g., about 50 μM or less, about 25 μM or less, about 10 μM or less, about 5 μM or less, or about 1 μM or less, in sodium mobilization and/or electrophysiological assays. In certain embodiments, Compounds of the Invention exhibit an $IC_{50}$ for $Na_v1.7$ of 100 μM or less, about 50 μM or less, about 25 μM or less, about 10 μM or less, about 5 μM or less, about 1 μM or less, about 0.5 μM or less, about 0.1 μM or less, about 0.05 μM or less, or about 0.01 μM or less. Compounds of the Invention can be tested for their $Na^+$ channel blocking activity using methods known in the art and by the following fluorescence imaging and electrophysiological in vitro assays and/or in vivo assays.

In one embodiment, Compounds of the Invention demonstrate substantially no penetration across the CNS blood-brain barrier in a mammal. Such compounds are referred to as "peripherally restricted" as a means to designate their PNS (peripheral nervous system) versus CNS (central nervous system) tissue selectivity.

In one embodiment, the PNS:CNS concentration ratio of a peripherally restricted Compound of the Invention is about 5:1, about 10:1, about 20:1, about 30:1; about 50:1; about 100:1, about 250:1, about 500:1, about 1000:1, about 5,000:1, about 10,000:1, or more. Compounds of the Invention can be tested for their ability to penetrate the central nervous system using in vitro and in vivo methods known in the art.

In Vitro Assay Protocols
FLIPR® Assays

Recombinant $Na_v1.7$ Cell Line: In vitro assays were performed in a recombinant cell line expressing cDNA encoding the alpha subunit ($Na_v1.7$, SCN9a, PN1, NE) of human $Na_v1.7$ (Accession No. NM_002977). The cell line was provided by investigators at Yale University (Cummins et al, *J. Neurosci.* 18(23): 9607-9619 (1998)). For dominant selection of the $Na_v1.7$-expressing clones, the expression plasmid co-expressed the neomycin resistance gene. The cell line was constructed in the human embryonic kidney cell line, HEK293, under the influence of the CMV major late promoter, and stable clones were selected using limiting dilution cloning and antibiotic selection using the neomycin analogue, G418. Recombinant beta and gamma subunits were not introduced into this cell line. Additional cell lines expressing recombinant $Na_v1.7$ cloned from other species can also be used, alone or in combination with various beta subunits, gamma subunits or chaperones.

Non-recombinant Cell Lines Expressing Native $Na_v1.7$: Alternatively, in vitro assays can be performed in a cell line expressing native, non-recombinant $Na_v1.7$, such as the ND7 mouse neuroblastoma X rat dorsal root ganglion (DRG) hybrid cell line ND7/23, available from the European Cell Culture Collection (Cat. No. 92090903, Salisbury, Wiltshire, United Kingdom). The assays can also be performed in other cell lines expressing native, non-recombinant $Na_v1.7$, from various species, or in cultures of fresh or preserved sensory neurons, such as dorsal root ganglion (DRG) cells, isolated from various species. Primary screens or counter-screens of other voltage-gated sodium channels can also be performed, and the cell lines can be constructed using methods known in the art, purchased from collaborators or commercial establishments, and they can express either recombinant or native channels. The primary counter-screen is for one of the central neuronal sodium channels, $Na_v1.2$ (rBIIa), expressed in HEK293 host cells (Ilyin et al., *Br. J. Pharmacol.* 144:801-812 (2005)). Pharmacological profiling for these counter-screens is carried out under conditions similar to the primary or alternative $Na_v1.7$ assays described below.

Cell Maintenance: Unless otherwise noted, cell culture reagents were purchased from Mediatech of Herndon, Va. The recombinant $Na_v1.7$/HEK293 cells were routinely cultured in growth medium consisting of Dulbecco's minimum essential medium containing 10% fetal bovine serum (FBS, Hyclone, Thermo Fisher Scientific, Logan, Utah), 100 U/mL penicillin, 100 μg/mL streptomycin, 2-4 mM L-glutamine, and 500 mg/mL G418. For natural, non-recombinant cell lines, the selective antibiotic was omitted, and additional media formulations can be applied as needed.

Assay Buffer: The assay buffer was formulated by removing 120 mL from a 1 L bottle of fresh, sterile $dH_2O$ (Mediatech, Herndon, Va.) and adding 100 mL of 10×HBSS that does not contain $Ca^{++}$ or $Mg^{++}$ (Gibco, Invitrogen, Grand Island, N.Y.) followed by 20 mL of 1.0 M Hepes, pH 7.3 (Fisher Scientific, BP299-100). The final buffer consisted of 20 mM Hepes, pH 7.3, 1.261 mM $CaCl_2$, 0.493 mM $MgCl_2$, 0.407 mM $Mg(SO)_4$, 5.33 mM KCl, 0.441 mM $KH_2PO_4$, 137 mM NaCl, 0.336 mM $Na_2HPO_4$ and 0.556 mM D-glucose (Hanks et al., *Proc. Soc. Exp. Biol. Med.* 71:196 (1949)), and the simple formulation was typically the basic buffer throughout the assay (i.e., all wash and addition steps).

CoroNa™ Green AM $Na^+$ Dye for Primary Fluorescence Assay: The fluorescence indicator used in the primary fluorescence assay was the cell permeant version of CoroNa™ Green (Invitrogen, Molecular Probes, Eugene, Oreg.), a dye that emits light in the fluorescence range (Harootunian et al., *J. Biol. Chem.* 264(32):19458-19467 (1989)). The intensity of this emission, but not the wavelength range, is increased when the dye is exposed to $Na^+$ ions, which it can bind with partial selectivity. Cells expressing $Na_v1.7$ or other sodium channels were loaded with the CoroNa™ Green dye immediately in advance of the fluorescence assay, and then, after agonist stimulation, the mobilization of $Na^+$ ions was detected as the $Na^+$ ions flowed from the extracellular fluid into the cytoplasm through the activated sodium channel pores. The dye was stored in the dark as a lyophilized powder, and then an aliquot was dissolved immediately before the cell loading procedure, according to the instructions of the manufacturer to a stock concentration of 10 mM in DMSO. It was then diluted in the assay buffer to a 4× concentrated working solution, so that the final concentration of dye in the cell loading buffer was 5 μM.

Membrane Potential Dye for Alternative Fluorescence Assays: A fluorescence indicator that can be used in alternative fluorescence assays is the blue version membrane potential dye (MDS, Molecular Devices, Sunnyvale, Calif.), a dye that detects changes in molecules following a change in membrane potential. An increase in fluorescence is expected if agonist stimulation provokes a change in membrane potential. Cells expressing $Na_v1.7$ or other sodium channels are incubated with the membrane potential dye 30-60 minutes before the fluorescence assay. In the case of the KCl pre-stimulation version of the assay, the dye and all other components are washed out immediately before the assay, and the dye is then replaced. In the version lacking KCl pre-stimulation, the dye remains on the cells and is not washed out or replaced. The dye is stored in the dark as a lyophilized powder, and then an aliquot dissolved in assay buffer to form a 20×-concentrated stock solution that can be used for several weeks.

Agonists: In the fluorescence assays, two agonists were used in combination, namely 1) veratridine; and 2) the venom from the yellow scorpion, *Leiurus quinquestriatus hebraeus*. Veratridine is an alkaloid small molecule that facilitates the capture of channel openings by inhibiting inactivation, and the scorpion venom is a natural preparation that includes peptide toxins selective for different subsets of voltage-gated sodium channels. These scorpion toxins inhibit the fast inactivation of their cognate target channels. Stock solutions of the agonists were prepared to 40 mM in DMSO (veratridine) and 1 mg/mL in $dH_2O$ (scorpion venom), and then diluted to make a 4× or 2× stock (depending on the particular assay) in assay buffer, the final concentration being 100 μM (veratridine) and 10 μg/mL (scorpion venom). Both of the agonists were purchased from Sigma Aldrich, St. Louis, Mo.

Test Compounds: Test compounds were dissolved in DMSO to yield 10 mM stock solutions. The stock solutions were further diluted using DMSO in 1:3 serial dilution steps with 10 points (10,000 μM, 3.333 μM, 1.111 μM, 370 μM, 123 μM, 41 μM, 14 μM, 4.6 μM, 1.5 μM and 0.5 μM). The stock solutions were further diluted in assay buffer (1:125) as 4× stock serial dilutions with a DMSO concentration of 0.8% (final [DMSO], in the assay, from the compounds component=0.2%), so that the compounds' final concentrations in the assay were 20 μM, 6.7 μM, 2.2 μM, 0.74 μM, 0.25 μM and 0.08 μM, 0.03 μM, 0.01 μM, 0.003 μM and 0.001 μM. If a particular test article appeared to be especially potent, then the concentration curve was adjusted, e.g., to 10-fold lower concentrations, in order to perform the dose-response in a more relevant concentration range. Compound dilutions were added during the dye-loading and pre-stimulation step, and then again during the fluorescence assay, early in the kinetic read. Compound dilutions were added in duplicate rows across the middle 80 wells of the 96-well plate, whereas the fully stimulated and the fully inhibited controls (positive and negative) were located in the top 4 side wells and the bottom 4 side wells, respectively, on the left and right sides of the assay plate.

Data Analysis: The data were analyzed according to methods known to those skilled in the art or using the GraphPad® Prism version 4.0 or higher, Program (available from GraphPad Prism® Software (version 4.0 or higher), San Diego, Calif.) to determine the $IC_{50}$ value for the test article. At least one standard reference compound was evaluated during each experiment.

FLIPR® or FLIPR$^{TETRA}$® Sodium Dye Assay with KCl and Test Article Pre-Incubation: Cells were prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate was then incubated in growth media, with or without selective antibiotic, overnight at 37° C. at 5% $CO_2$, 95% humidity, in preparation for the assay. For counter-screens of other voltage-gated sodium channels, the procedure was very similar, though optimal densities of cells, media and subsequent assay components can be fine-tuned for the particular cell line or isoform.

The next day, at the start of the assay, the media was flicked from the cells and the wells were washed once with 50 μl/well assay buffer (1× Hank's balanced salt solution without sodium bicarbonate or phenol red, 20 mM Hepes, pH 7.3) and then pre-incubated with the test articles, CoroNa™ Green AM sodium dye (for cell loading) and KCl for re-polarization and synchronization of the channels in the entire population of cells. For this dye-loading and pre-stimulation step, the components were added as follows, immediately after the wash step: 1) first, the compound dilutions and controls were added as 4× concentrates in assay buffer at 50 μL/well; 2) CoroNa™ Green AM dye was diluted from the stock solution to 20 μM in assay buffer (4× concentrate) and added to the plate at 50 μL/well; and 3) finally, a solution of 180 mM KCl (2×) was prepared by diluting a 2M stock solution into assay buffer and the solution was added to the cells at 100 μl/well. The cells were incubated at 25° C. in the dark for 30 min. before their fluorescence was measured.

The plates containing dye-loaded cells were then flicked to remove the pre-incubation components and washed once with 100 μL/well assay buffer. A 100 μL/well aliquot of assay buffer was added back to the plate, and the real-time assay was commenced. The fluorescence of cells was measured using a fluorescence plate reader (FLIPR$^{TETRA}$® or FLIPR384®, MDS, Molecular Devices, Sunnyvale, Calif.) Samples were excited by either a laser or a PMT light source (Excitation wavelength=470-495 nM) and the emissions were filtered (Emission wavelength=515-575 nM). The additions of compound and the channel activators in this cell-based, medium-to-high throughput assay were performed on the fluorescence plate reader and the results (expressed as relative fluorescence units) were captured by means of camera shots every 1-3 sec., then displayed in real-time and stored. Generally, there was a 15 sec. base line, with camera shots taken every 1.5 sec., then the test compounds were added, then another 120 sec. baseline was conducted, with camera shots taken every 3 sec.; and finally, the agonist solution (containing veratridine and scorpion venom) was added. The amplitude of fluorescence increase, resulting from the binding of $Na^+$ ions to the CoroNa™ Green dye, was captured for ~180 sec. thereafter. Results were expressed in relative fluorescence units (RFU) and were determined by using the maximum signal during the latter part of the stimulation; or the maximum minus the minimum during the whole agonist stimulation period; or by taking the area under the curve for the whole stimulation period.

The assay was performed as a screening assay as well with the test articles present in standard amounts (e.g., 10 μM) in only one or two wells of a multi-well plate during the primary screen. Hits in this screen were typically profiled more exhaustively (multiple times), subjected to dose-response or competition assays and tested in counter screens against other voltage-gate sodium channels or other biologically relevant target molecules.

FLIPR® or FLIPR$^{TETRA}$® Membrane Potential Assay with KCl and Test Article Pre-Incubation: Cells are prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% $CO_2$, 95% humidity, in preparation for the assay (see, e.g., Benjamin et. al., J. Biomol. Screen 10(4):365-373 (2005)). For screens and counter-screens of other voltage-gated sodium channels, the assay protocol is similar, though optimal densities of cells, media and subsequent assay components can be fine-tuned for the particular cell line or sodium channel isoform being tested.

The next day, at the start of the assay, the media is flicked from the cells and the wells are washed once with 50 μL/well assay buffer (1× Hank's balanced salt solution without sodium bicarbonate or phenol red, 20 mM Hepes, pH 7.3) and then pre-incubated with the test articles, the membrane potential dye (for cell loading), and the KCl for re-polarization and synchronization of the channels in the entire population of cells. For this dye-loading and pre-stimulation step, the components are added as follows, immediately after the wash step: 1) first, the compound dilutions and controls are added as 4× concentrates in assay buffer at 50 μL/well; 2) membrane potential dye is diluted from the stock solution in assay buffer (4× concentrate) and added to the plate at 50 μL/well; and 3) finally, a solution of 180 mM KCl (2×) is prepared by diluting a 2M stock solution into assay buffer and the solution added to the cells at 100 μL/well. The cells are incubated at 37° C. in the dark for 30-60 min. before their fluorescence is measured.

The plates containing dye-loaded cells are then flicked to remove the pre-incubation components and washed once with 50 μL/well assay buffer. A 50 μL/well aliquot of membrane potential dye is added back to the plate, and the real-time assay is commenced. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first) and then the channel activators (later) in this are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well with the test articles present in standard amounts (e.g., 10 µM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

FLIPR® or FLIPR$^{TETRA}$® Sodium Dye Assay without KCl and Test Article Pre-Incubation: Cells are prepared by plating the recombinant HEK293 cells or other host cells expressing either recombinant or non-recombinant, native, Na$_v$1.7 alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% $CO_2$, 95% humidity, in preparation for the assay. For counter-screens of other voltage-gated sodium channels, the procedure is very similar, though optimal densities of cells, media and subsequent assay components can be fine-tuned for the particular cell line or isoform.

The next day, at the start of the assay, the media is flicked from the cells and the wells washed once with 50 µL/well assay buffer (1× Hank's balanced salt solution without sodium bicarbonate or phenol red, 20 mM Hepes, pH 7.3). Membrane potential dye is then added to each well of the 96-well plate (50 µL/well), from a freshly diluted sample of the stock (now at 4× concentration) in the assay buffer. The cells are incubated at 37° C. in the dark for 30-60 min. before their fluorescence is measured.

In this standard membrane potential assay, the 96-well plate containing dye-loaded cells is then loaded directly onto the plate reader without aspirating the dye solution and without any further washing of the cells. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first, 50 µL/well from a 4× stock plate) and then the channel activators (later, 100 µL/well from a 2× stock solution) in this kinetic assay are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well, with the test articles present in standard amounts (e.g. 10 µM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

Electrophysiology Assay

Cells: The hNa$_v$1.7 expressing HEK-293 cells are plated on 35 mm culture dishes pre-coated with poly-D-lysine in standard DMEM culture media (Mediatech, Inc., Herndon, Va.) and incubated in a 5% $CO_2$ incubator at 37° C. Cultured cells are used approximately 12-48 hours after plating.

Electrophysiology: On the day of experimentation, the 35 mm dish is placed on the stage of an inverted microscope equipped with a perfusion system that continuously perfuses the culture dish with fresh recording media. A gravity driven superfusion system is used to apply test solutions directly to the cell under evaluation. This system consists of an array of glass pipettes connected to a motorized horizontal translator. The outlet of the shooter is positioned approximately 100 µm from the cell of interest.

Whole cell currents are recorded using the whole-cell patch clamp configuration using an Axopatch 200B amplifier (Axon Instruments, Foster City Calif.), 1322A A/D converter (Axon Instruments) and pClamp software (v. 8; Axon Instruments) and stored on a personal computer. Gigaseals are formed and the whole-cell configuration is established in voltage clamp mode, and membrane currents generated by hNa$_v$1.7 are recorded in gap-free mode. Borosilicate glass pipettes have resistance values between 1.5 and 2.0 MΩ when filled with pipette solution and series resistance (<5 MΩ) is compensated 75-80%. Signals are sampled at 50 kHz and low pass filtered at 3 kHz.

Voltage Protocols: After establishing the whole-cell configuration in voltage clamp mode, voltage protocols are run to establish the 1) test potential, 2) holding potential, and 3) the conditioning potential for each cell.

After establishing the whole-cell configuration in voltage clamp mode, a standard I-V protocol is run to determine the potential at which the maximal current ($I_{max}$) is elicited. This potential is the test potential ($V_t$). To determine a conditioning potential at which 100% of channels are in the inactivated state, a standard steady-state inactivation (SSIN) protocol is run using a series of fifteen 100 ms-long depolarizing prepulses, incrementing in 10 mV steps, immediately followed by a 5 ms testing pulse, $V_t$, to $V_{max}$. This protocol also permits determination of the holding potential at which all channels are in the resting state.

For compounds causing significant retardation of recovery from inactivation, an estimate of the affinity for the inactivated state of the channel ($K_i$) is generated using the following protocol. From the negative, no residual inactivation, holding potential, the cell is depolarized to the conditioning voltage for 2-5 seconds, returned to the negative holding potential for 10-20 ms to relieve fast inactivation and then depolarized to the test potential for ~15 ms. This voltage protocol is repeated every 10-15 seconds, first to establish a baseline in the absence of the test compound, then in the presence of the test compound.

After a stable baseline is established, the test compound is applied and block of the current elicited by the test pulse assessed. In some cases, multiple cumulative concentrations are applied to identify a concentration that blocked between 40-60% of this current. Washout of the compound is attempted by superfusing with control solution once steady-state block is observed. An estimate of the $K_i$ is calculated as follows:

$$K_i=[\text{drug}]*\{FR/(1-FR)\}, \qquad \text{Eq. 1}$$

where [drug] is the concentration of a drug, and $$FR=I(\text{after drug})/I(\text{control}), \qquad \text{Eq. 2}$$

where I is the peak current amplitude. If multiple concentrations are used, $K_i$ is determined from the fit of a logistic equation to FRs plotted against corresponding drug concentrations.

In the alternative, the voltage clamp protocol to examine hNa$_v$1.7 currents is as follows. First, the standard current-voltage relationship is tested by pulsing the cell from the holding voltage ($V_h$) of −120 mV by a series of 5 msec long square-shaped test pulses incrementing in +10 mV steps over the membrane voltage range of −90 mV to +60 mV at the pace of stimulation of 0.5 Hz. This procedure determines the voltage that elicits the maximal current ($V_{max}$). Second, $V_h$ is re-set to −120 mV and a steady-state inactivation (SSIN) curve is taken by the standard double-pulse protocol: 100 ms depolarizing pre-pulse is incremented in steps of +10 mV (voltage range from −90 mV to 0 mV) immediately followed by the 5 ms long test pulse to −10 mV at the pace of stimulation of 0.2 Hz. This procedure determines the voltage of full inactivation ($V_{full}$). Third, the cell is repeatedly stimulated with the following protocol, first in the absence of the test compound then in its presence. The protocol consists of depolarizing the cell from the holding potential of −120 mV to the $V_{full}$ value for 4.5 seconds then repolarizing the cell to the holding potential for 10 ms before applying the test pulse to the $V_{max}$ for 5 ms. The amount of inhibition produced by the test compound is determined by comparing the current amplitude elicited by the test pulse in the absence and presence of the compound.

In a further alternative, the voltage clamp protocol to examine hNa$_v$1.7 currents is as follows. After establishing the whole-cell configuration in voltage clamp mode, two voltage protocols are run to establish: 1) the holding potential; and 2) the test potential for each cell.

Resting Block: To determine a membrane potential at which the majority of channels are in the resting state, a standard steady-state inactivation (SSIN) protocol is run using 100 ms prepulses×10 mV depolarizing steps. The holding potential for testing resting block (Vh$_1$) is 20 mV more hyperpolarized than the first potential where inactivation is observed with the inactivation protocol.

From this holding potential a standard I-V protocol is run to determine the potential at which the maximal current (Imax) is elicited. This potential is the test potential (Vt).

The compound testing protocol is a series of 10 ms depolarizations from the Vhi (determined from the SSIN) to the Vt (determined from the I-V protocol) repeated every 10-15 seconds. After a stable baseline is established, a high concentration of a test compound (highest concentration solubility permits or that which provides ~50% block) is applied and block of the current assessed. Washout of the compound is attempted by superfusing with control solution once steady-state block is observed. The fractional response is calculated as follows:

$$K_r=[\text{drug}]*\{FR/(1-FR)\}, \qquad \text{Eq. 3}$$

where [drug] is the concentration of a drug, and $$FR=I(\text{after drug})/I(\text{control}), \qquad \text{Eq. 2}$$

where I is the peak current amplitude and is used for estimating resting block dissociation constant, $K_r$.

Block of Inactivated Channels: To assess the block of inactivated channels the holding potential is depolarized such that 20-50% of the current amplitude is reduced when pulsed to the same Vt as above. The magnitude of this depolarization depends upon the initial current amplitude and the rate of current loss due to slow inactivation. This is the second holding potential (Vh$_2$). The current reduction is recorded to determine the fraction of available channels at this potential (h).

$$h=I\,@Vh2/I\text{max}. \qquad \text{Eq. 4}$$

At this membrane voltage a proportion of channels is in the inactivated state, and thus inhibition by a blocker includes interaction with both resting and inactivated channels.

To determine the potency of the test compound on inactivated channels, a series of currents are elicited by 10 ms voltage steps from Vh2 to Vt every 10-15 seconds. After establishing a stable baseline, the low concentration of the compound is applied. In some cases, multiple cumulative concentrations will have to be applied to identify a concentration that blocks between 40-60% of the current. Washout is attempted to re-establish baseline. Fractional responses are measured with respect to a projected baseline to determine $K_{app}$.

$$K_{app}=[\text{drug}]*\{FR/(1-FR)\}, \qquad \text{Eq. 5}$$

where [drug] is the concentration of a drug.

This $K_{app}$ value, along with the calculated $K_r$ and h values, are used to calculate the affinity of the compound for the inactivated channels ($K_i$) using the following equation:

$$K_i=(1-h)/((1/K_{app})-(h/K_r)). \qquad \text{Eq. 6}$$

Solutions and Chemicals: For electrophysiological recordings the external solution is either standard, DMEM supplemented with 10 mM HEPES (pH adjusted to 7.34 with NaOH and the osmolarity adjusted to 320) or Tyrodes salt solution (Sigma, USA) supplemented with 10 mM HEPES (pH adjusted to 7.4 with NaOH; osmolarity=320). The internal pipette solution contained (in mM): NaCl (10), CsF (140), CaCl$_2$ (1), MgCl$_2$ (5), EGTA (11), HEPES (10: pH 7.4, 305 mOsm). Compounds are prepared first as series of stock solutions in DMSO and then dissolved in external solution; DMSO content in final dilutions do not exceed 0.3%. At this concentration, DMSO does not affect sodium currents. Vehicle solution used to establish base line contains 0.3% DMSO.

Data Analysis: Data is analyzed off-line using Clampfit software (pClamp, v. 8; Axon Instruments) and graphed using GraphPad Prism® (v: 4.0 or higher) software.

In Vivo Assay for Pain

Compounds of the Invention can be tested for their antinociceptive activity in the formalin model as described in Hunskaar et al., *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period, mice are weighed and given either the compound of interest administered i.p. or p.o., or the appropriate volume of vehicle (for example, 10% Tween-80 or 0.9% saline, and other pharmaceutically acceptable vehicles) as control. Fifteen minutes after the i.p. dosing, and 30 minutes after the p.o. dosing mice are injected with formalin (20 µL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

In Vivo Assays for Inflammatory or Neuropathic Pain

Test Animals: Each experiment uses rats weighing between 200-260 g at the start of the experiment. The rats are group-housed and have free access to food and water at all times, except prior to oral administration of a test compound when food is removed for 16 h before dosing. A control group acts as a comparison to rats treated with a Compound of the Invention. The control group is administered the carrier as used for the test compound. The volume of carrier administered to the control group is the same as the volume of carrier and test compound administered to the test group.

Inflammatory Pain: To assess the actions of Compounds of the Invention on the treatment of inflammatory pain the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (Bartho et al., *Naunyn-Schmiedeberg's Archives of Pharmacol.* 342:666-670 (1990)). The left hind paw of each animal is administered a 50 µL intraplantar injection of 50% FCA. 24 hour post injection, the animal is assessed for response to noxious mechanical stimuli by determining the paw withdrawal threshold (PWT), or to noxious thermal stimuli by determining the paw withdrawal latency (PWL), as described below. Rats are then administered a single injection of either a test compound or 30 mg/Kg of a positive control compound (such as indomethacin, Celebrex, or naproxen sodium), or an equal volume of vehicle as a negative control. Responses to noxious mechanical or thermal stimuli are then determined 1, 3, 5 and 24 hours post administration (admin). Percentage reversal of hyperalgesia for each animal is defined as:

$$\% \text{ reversal} = \frac{\left[\begin{array}{c}(\text{post administration } PWT \text{ or } PWL) - \\ (\text{pre-administration } PWT \text{ or } PWL)\end{array}\right]}{\left[\begin{array}{c}(\text{baseline } PWT \text{ or } PWL) - \\ (\text{pre-administration } PWT \text{ or } PWL)\end{array}\right]} \times 100$$

Neuropathic Pain: To assess the actions of the test compounds for the treatment of neuropathic pain the Seltzer model or the Chung model can be used.

In the Seltzer model, the partial sciatic nerve ligation model of neuropathic pain is used to produce neuropathic hyperalgesia in rats (Seltzer et al., *Pain* 43:205-218 (1990)). Partial ligation of the left sciatic nerve is performed under isoflurane/$O_2$ inhalation anesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a 3/8 curved, reversed-cutting mini-needle and tightly ligated so that the dorsal 1/3 to 1/2 of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after drug administration for the ipsilateral (same side as the injury) rear paw of the animal. Percentage reversal of neuropathic hyperalgesia is defined as:

$$\% \text{ reversal} = \frac{\left[\begin{array}{c}(\text{post administration } PWT) - \\ (\text{pre-administration } PWT)\end{array}\right]}{\left[\begin{array}{c}(\text{baseline } PWT) - \\ (\text{pre-administration } PWT)\end{array}\right]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anesthesia. Following induction of anesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is (are) isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is (are) not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention for the left rear paw of the animal. The animals can also be assessed for response to noxious thermal stimuli or for tactile allodynia, as described below. The Chung model for neuropathic pain is described in Kim et al., *Pain* 50(3):355-363 (1992).

Tactile Allodynia: Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hind paw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia: Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia associated with nerve injury. In another non-limiting embodiment, mechanical hyperalgesiaq associated with inflammatory pain can be assessed in rats. Rats are tested prior to induction of inflammation (such as by intraplantar injection of FCA) to determine a baseline, or normal PWT. Rats are tested again 24 hours after FCA injection, prior to, and at different times after (e.g. 1, 3, 5, and 24 hr) drug administration. An increase in PWT following drug administration indicates that the test compound reduces mechanical hyperalgesia associated with inflammation.

In Vivo Assay for Anticonvulsant Activity

Compounds of the Invention can be tested for in vivo anticonvulsant activity after i.v., p.o., or i.p. injection using any of a number of anticonvulsant tests in mice or rats, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

Pharmaceutical Compositions

Compounds of the Invention can be administered to a mammal in the form of a raw chemical without any other components present. More preferably, however, Compounds of the Invention are administered to a mammal as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present disclosure include all compositions where a Compound of the Invention is combined with one or more pharmaceutically acceptable carriers. In one embodiment, the Compound of the Invention is present in the composition in an amount that is effective to achieve its intended therapeutic purpose when administered to a mammal in need of such treatment. While individual needs may vary, a determination of optimal ranges of effective amounts of each compound is within the skill of the art. Typically, a Compound of the Invention can be administered to a mammal, e.g., a human, orally at a dose of from about 0.0025 to about 1500 mg per kg body weight of the mammal, or an equivalent amount of a pharmaceutically acceptable salt, or solvate thereof, per day to treat the particular disorder. A useful oral dose of a Compound of the Invention administered to a mammal is from about 0.0025 to about 50 mg per kg body weight of the mammal, or an equivalent amount of the pharmaceutically acceptable salt, or solvate thereof. For intramuscular injection, the dose is typically about one-half of the oral dose.

A unit oral dose may comprise from about 0.01 mg to about 1 g of the Compound of the Invention, e.g., about 0.01 mg to about 500 mg, about 0.01 mg to about 250 mg, about 0.01 mg to about 100 mg, 0.01 mg to about 50 mg, e.g., about 0.1 mg to about 10 mg, of the compound. The unit dose can be administered one or more times daily, e.g., as one or more tablets or capsules, each containing from about 0.01 mg to about 1 g of the compound, or an equivalent amount of a pharmaceutically acceptable salt or solvate thereof.

A pharmaceutical composition of the present disclosure can be administered to any animal that may experience the beneficial effects of a Compound of the Invention. Foremost among such animals are mammals, e.g., humans and companion animals, although the disclosure is not intended to be so limited.

A pharmaceutical composition of the present disclosure can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

Pharmaceutical compositions of the invention can take the form of solutions, suspensions, emulsions, tablets, pills, pellets, multi-particulates, capsules, capsules containing liquids, capsules containing powders, capsules containing multi-particulates, lozenges, sustained-release formulations, thin films, suppositories, aerosols, sprays, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference. In one embodiment, a pharmaceutical composition of the present disclosure can be administered orally and is formulated into tablets, dragees, capsules or an oral liquid preparation. In one embodiment, the oral formulation comprises extruded multiparticulates comprising the Compound of the Invention.

Alternatively, a pharmaceutical composition of the present disclosure can be administered rectally, and is formulated in suppositories.

Alternatively, a pharmaceutical composition of the present disclosure can be administered by injection.

Alternatively, a pharmaceutical composition of the present disclosure can be administered transdermally.

Alternatively, a pharmaceutical composition of the present disclosure can be administered by inhalation or by intranasal or transmucosal administration.

Alternatively, a pharmaceutical composition of the present disclosure can be administered by the intravaginal route.

A pharmaceutical composition of the present disclosure can contain from about 0.01 to 99 percent by weight, and preferably from about 0.25 to 75 percent by weight, of active compound(s).

A method of the present disclosure, such as a method of treating a disorder responsive to the blockade of sodium channels in a mammal in need thereof, can further comprise administering a second therapeutic agent to the mammal in combination with a Compound of the Invention. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

Compounds of the Invention (i.e., the first therapeutic agent) and the second therapeutic agent can act additively or, in one embodiment, synergistically. Alternatively, the second therapeutic agent can be used to treat a disorder or condition that is different from the disorder or condition for which the first therapeutic agent is being administered, and which disorder or condition may or may not be a condition or disorder as defined herein. In one embodiment, a Compound of the Invention is administered concurrently with a second therapeutic agent; for example, a single composition comprising both an effective amount of a Compound of the Invention and an effective amount of the second therapeutic agent can be administered. Accordingly, the present disclosure further provides a pharmaceutical composition comprising a combination of a Compound of the Invention, the second therapeutic agent, and a pharmaceutically acceptable carrier. Alternatively, a first pharmaceutical composition comprising an effective amount of a Compound of the Invention and a second pharmaceutical composition comprising an effective amount of the second therapeutic agent can be concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating a disorder or condition.

The second therapeutic agent can be an opioid agonist, a non-opioid analgesic, a non-steroidal anti-inflammatory agent, an antimigraine agent, a Cox-II inhibitor, a $\beta$-adrenergic blocker, an anticonvulsant, an antidepressant, an anti-cancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol. II 1196-1221 (A. R. Gennaro ed. 19th ed. 1995) which are hereby incorporated by reference in their entireties.

A pharmaceutical composition of the present disclosure is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions, and methods of the present disclosure. Suitable modifications and adaptations of the variety of conditions and parameters normally encountered in clinical therapy and which are obvious to those skilled in the art in view of this disclosure are within the spirit and scope of the disclosure.

EXAMPLES

Example 1

Synthesis of Compound 12

Scheme 2

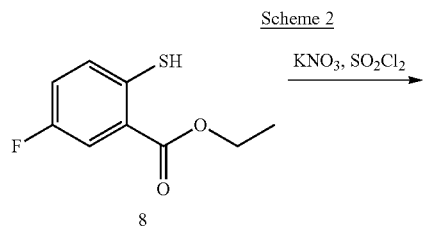

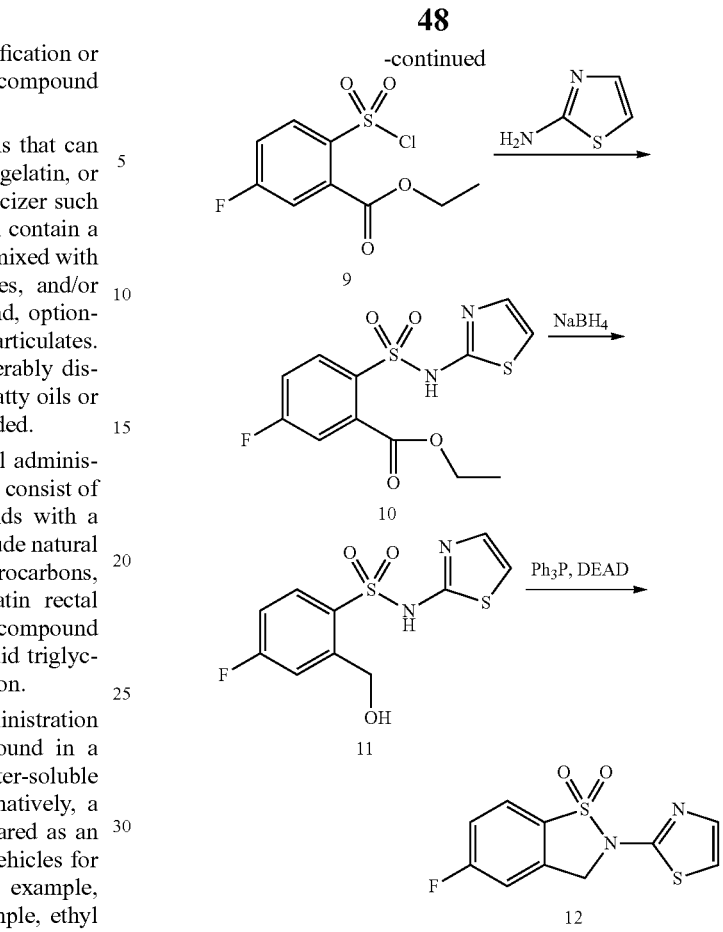

To a mixture of compound 8 (3.334 g, 16.65 mmol, 1 eq) in acetonitrile (40 mL) was added KNO$_3$ (4.210 g, 41.64 mmol, 2.5 eq). The mixture was cooled on an ice bath, then a solution of sulfuryl chloride (3.40 mL, 41.94 mmol, 2.5 eq.) in acetonitrile (10 mL) was added dropwise over ~4 minutes. After 10 minutes, the ice bath was removed and the reaction was stirred at ambient temperature overnight. The reaction mixture was partitioned between 250 mL Et$_2$O and 50 mL saturated NaHCO$_3$, and the organics were isolated and washed successively with 50 mL saturated NaHCO$_3$ and 50 mL brine. The organics were dried with MgSO$_4$, filtered and evaporated in vacuo to give compound 9 as a yellow crystalline solid (4.528 g, quant.). LC/MS, m/z=267 [M+H]$^+$ (Calc: 266).

To a mixture of compound 9 (3.151 g, 11.82 mmol, 1 eq) and 2-aminothiazole (2.370 g, 23.67 mmol, 2 eq.) was added 1:1 pyridine/DCM (40 mL). After one hour of stirring at ambient temperature, the mixture was heated at reflux overnight. The reaction mixture was evaporated in vacuo, diluted with acetone, evaporated in vacuo again, diluted once more with MeOH, and evaporated in vacuo. The residue was chromatographed over silica gel with 25-75% acetone in hexanes. The product fractions were evaporated in vacuo to give compound 10 as a pink-range powder (1.750 g, 5.30 mmol, 45% yield). LC/MS, m/z=331 [M+H]$^+$ (Calc: 330).

To a mixture of compound 10 (1.750 g, 5.30 mmol, 1 eq) in THF (50 mL) was added NaBH$_4$ (1.223 g, 32.33 mmol) and MeOH (10 mL). The mixture was heated at reflux for 1.5 hours then additional NaBH$_4$ (1.015 g, 26.83 mmol) was added. After two more hours, additional NaBH$_4$ (1.008 g, 26.65 mmol) was added. Lastly, after one hour, additional NaBH$_4$ (1.008 g, 26.65 mmol) was added, and the reaction was stirred at reflux overnight. After cooling, the solids were filtered off and rinsed with Et$_2$O. MeOH was added to the filtrate the diluted filtrate was evaporated in vacuo. The residue was partitioned between 200 mL EtOAc and 25 mL saturated NH$_4$Cl, and the organics were isolated and washed successively with 25 mL water then 25 mL brine. The organics were dried with MgSO$_4$, filtered and evaporated in vacuo. The residue was taken up in a smaller amount of EtOAc and filtered again to remove turbidity. The filtrate was evaporated in vacuo to give compound 11 (1.433 g, 4.97 mmol, 94%). LC/MS, m/z=289 [M+H]$^+$ (Calc: 288).

To a mixture of triphenyl phosphine (1.564 g, 5.96 mmol, 1.2 eq) in THF (20 mL) was added DEAD (2.70 mL, 40% solution in toluene, 5.94 mmol, 1.2 eq). The reaction was stirred for 2 minutes then added to a solution of compound 11 (1.433 g, 4.97 mmol, 1 eq) in THF (40 mL). After 30 minutes, the reaction was diluted with MeOH, evaporated in vacuo, and chromatographed over silica gel with 25-75% acetone in hexanes. The product fractions were evaporated in vacuo and the residue triturated with 5 mL acetone. The solid product was collected via filtration and rinsed once with 1 mL acetone. A second crop of product was obtained by evaporation of the filtrate in vacuo, triturating the residue with 4 mL MeOH, filtering off the resulting solid, and rinsing with 1 mL MeOH. Both crops of solid were combined and dried under vacuum at 40° C. to give compound 12 as a pale tan powder (0.614 g, 2.27 mmol, 46% yield). $^1$H NMR $\delta_H$ (400 MHz, DMSO-d$_6$) 7.87 (dd, J=8.8, 5.5 Hz, 1H), 7.55 (dd, J=9.0, 2.6 Hz, 1H), 7.48 (dt, J=8.8, 2.6 Hz, 1H), 7.28 (d, J=4.8 Hz, 1H), 6.97 (d, J=4.8 Hz, 1H), 5.66 (s, 2H); LC/MS, m/z=271 [M+H]$^+$ (Calc: 270).

Example 2

Synthesis of Compound 17

Compound 13 (10.003 g, 59.49 mmol, 1 eq.) was cooled on an ice-salt bath. To this was added chlorosulfonic acid (45 mL, 677 mmol, 11 eq.) dropwise over ~45 minutes. The ice bath was allowed to melt and the reaction warmed up and stirred overnight. The reaction mixture was then carefully poured onto ~500 g ice chips then extracted three times with 200 mL DCM. The combined organics were washed once with 50 mL saturated NaHCO$_3$ then once with 50 mL brine. The organics were dried with MgSO$_4$, filtered and evaporated in vacuo to give compound 14 as a tan crystalline solid (8.06 g, 30.22 mmol, 51% yield). LC/MS, m/z=267 [M+H]$^+$ (Calc: 266).

To a mixture of compound 14 (8.06 g, 30.22 mmol, 1 eq) and 2-aminothiazole (6.060 g, 60.52 mmol, 2 eq) was added 1:1 pyridine/DCM (100 mL). The mixture was heated at reflux for 2 days then quenched with MeOH and evaporated in vacuo. The residue was partitioned between 200 mL EtOAc and 50 mL 1N HCl which caused a solid to form. The solid was collected via filtration and washed once with 10 mL MeOH. The material was dried under vacuum at ~40-50° C. to give compound 15 as a peach-colored powder (4.73 g, 14.3 mmol, 47% yield). LC/MS, m/z=331 [M+H]$^+$ (Calc: 330).

To a mixture of compound 15 (4.73 g, 14.3 mmol, 1 eq) in THF (100 mL) was added NaBH$_4$ (3.259 g, 86.15 mmol, 6 eq) and MeOH (10 mL). The mixture was heated at reflux for 3 days. MeOH was added to the reaction mixture then it was evaporated in vacuo. The residue was partitioned between 250 mL EtOAc and 100 mL 10% citric acid solution. The organics were isolated and washed once with 50 mL brine. The organics were dried with Na$_2$SO$_4$, filtered and evaporated in vacuo to give compound 16 which was carried on as-is.

To a mixture of triphenyl phosphine (4.517 g, 17.22 mmol, 1.2 eq) in THF (25 mL) was added DEAD (7.9 mL, 40% solution in toluene, 17.4 mmol, 1.2 eq). The reaction Scheme 3

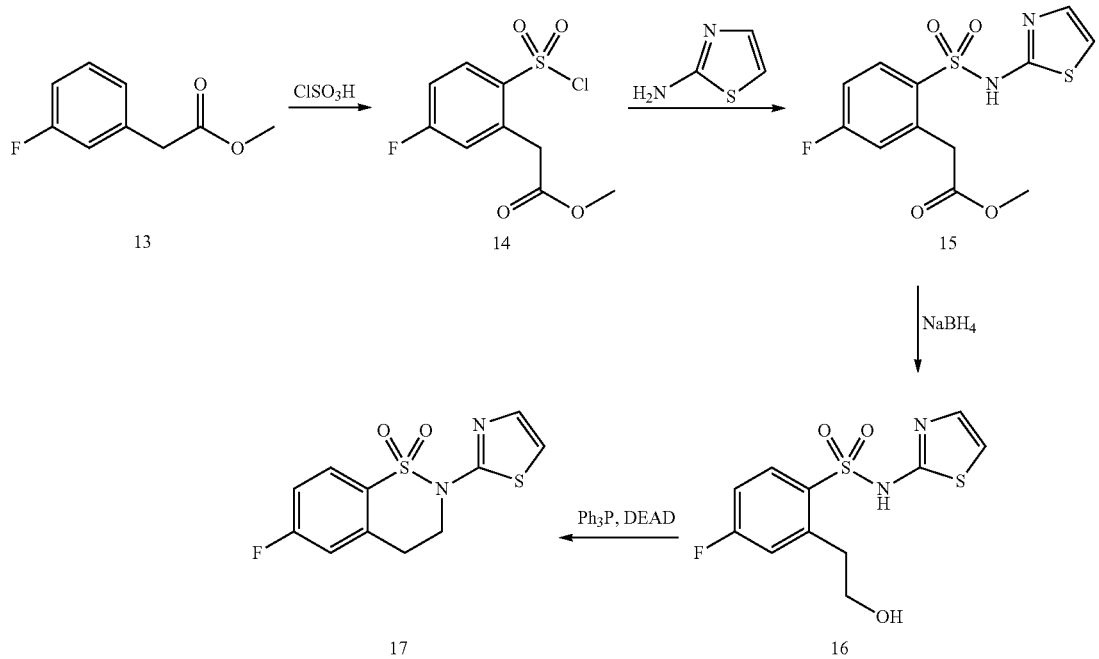

was stirred for 2 minutes then added to a solution of compound 16 (assume 14.3 mmol, 1 eq) in THF (75 mL). After two hours, to a mixture of triphenyl phosphine (2.260 g, 8.62 mmol, 0.6 eq) in THF (20 mL) was added DEAD (3.9 mL, 40% solution in toluene, 8.6 mmol, 0.6 eq). This was stirred for 2 minutes then added to the main reaction mixture. The reaction was stirred overnight then evaporated in vacuo. The residue was chromatographed over silica gel with 0-50% EtOAc in hexanes. The product fractions were evaporated in vacuo and the residue dried under vacuum at 30° C. to give the product 17 as a pale pink powder (2.239 g, 7.88 mmol, 55% yield). $^1$H NMR $\delta_H$ (400 MHz, DMSO-$d_6$) 7.95 (dd, J=8.8, 5.5 Hz, 1H), 7.53 (d, J=3.5 Hz, 1H), 7.41 (d, J=3.5 Hz, 1H), 7.40-7.31 (m, 2H), 4.58 (t, J=6.1 Hz, 2H), 3.33 (t, J=6.4 Hz, 2H). LC/MS, m/z=285 [M+H]$^+$ (Calc: 284).

Example 3

Synthesis of Compound 18

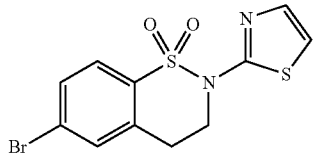

18

In a similar manner used to prepare compound 17, compound 18 was prepared starting from methyl 2-(3-bromophenyl)acetate rather than methyl 2-(3-fluorophenyl)acetate. $^1$H NMR $\delta_H$ (400 MHz, DMSO-$d_6$) 7.82-7.75 (m, 2H), 7.68 (dd, J=8.6, 2.2 Hz, 1H), 7.53 (d, J=3.5 Hz, 1H), 7.42 (d, J=3.7 Hz, 1H), 4.57 (t, J=6.1 Hz, 2H), 3.31 (t, J=6.1 Hz, 2H). LC/MS, m/z=345 [M+H]$^+$ (Calc: 344).

Example 4

Synthesis of Compound 5

Scheme 4

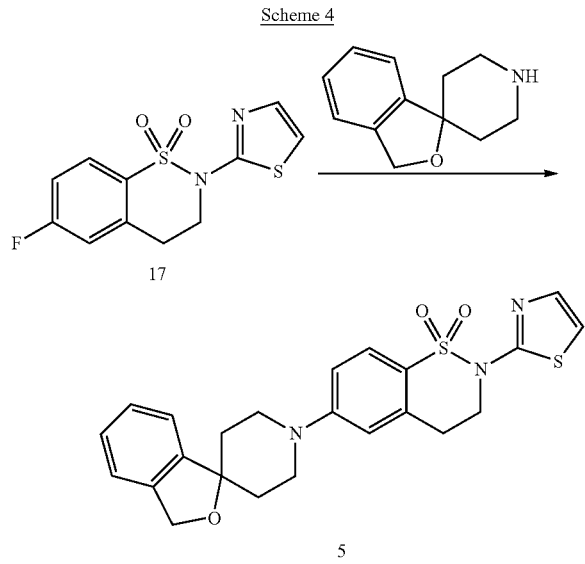

A mixture of compound 17 (0.143 g, 0.503 mmol, 1 eq), 3H-spiro[isobenzofuran-1,4'-piperidine]hydrochloride (0.127 g, 0.563 mmol, 1.1 eq), and iPr$_2$NEt (0.19 mL, 1.09 mmol, 2.2 eq) in acetonitrile (5 mL) was heated in a sealed pressure reaction bottle at 100° C. for 4 days. The reaction was approximately half converted at this point. The reaction was concentrated in vacuo and the residue chromatographed over silica gel with 20-50% EtOAc in hexanes. The product fractions were evaporated in vacuo. The residue was triturated with hexanes and hexanes containing a small amount of EtOAc, then dried under vacuum at 40° C. to give compound 5 as a cream-colored powder (0.064 g, 0.14 mmol, 28% yield). $^1$H NMR $\delta_H$ (400 MHz, DMSO-$d_6$) 7.60 (d, J=9.0 Hz, 1H), 7.50 (d, J=3.5 Hz, 1H), 7.35 (d, J=3.5 Hz, 1H), 7.31-7.21 (m, 4H), 7.02 (dd, J=6.4, 2.6 Hz, 1H), 6.93 (d, J=2.4 Hz, 1H), 5.03 (s, 2H), 4.55 (t, J=6.4 Hz, 2H), 3.94-3.86 (m, 2H), 3.26-3.16 (m, 4H), 1.93 (dt, J=12.9, 4.2 Hz, 2H), 1.68 (d, J=12.7 Hz, 2H). LC/MS, m/z=454 [M+H]$^+$ (Calc: 453).

Example 5

Synthesis of Compound 4

Scheme 4

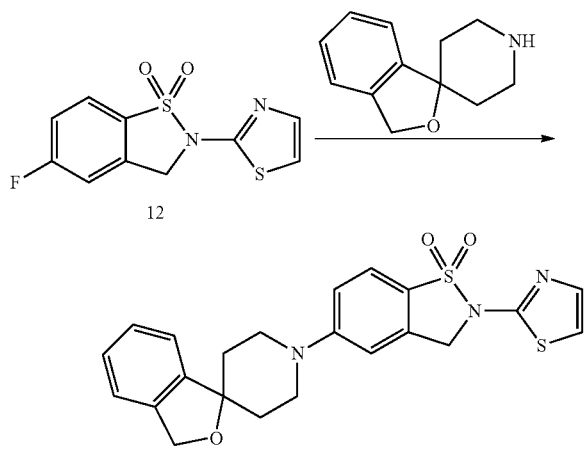

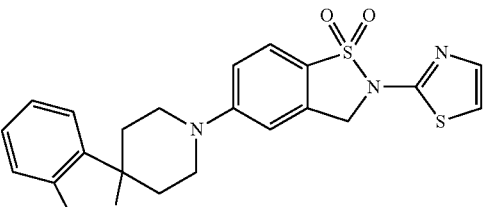

4

A mixture of compound 12 (0.136 g, 0.503 mmol, 1 eq), 3H-spiro[isobenzofuran-1,4'-piperidine]hydrochloride (0.128 g, 0.567 mmol, 1.1 eq), and iPr$_2$NEt (0.19 mL, 1.09 mmol, 2.2 eq) in acetonitrile (5 mL) were heated in a sealed pressure reaction bottle at 100° C. for 4 days. The reaction was approximately half converted at this point. The reaction was concentrated in vacuo and the residue chromatographed over silica gel with 25-75% acetone in hexanes. The product fractions were evaporated in vacuo. The residue was triturated with hexanes, filtered, then dried under vacuum at 40° C. to give compound 4 as a cream-colored powder (0.043 g, 0.10 mmol, 19% yield). $^1$H NMR $\delta_H$ (400 MHz, DMSO-$d_6$) 7.58 (d, J=9.0 Hz, 1H), 7.32-7.24 (m, 4H), 7.24-7.19 (m, 2H), 7.09 (dd, J=8.8, 2.4 Hz, 1H), 6.89 (d, J=4.8 Hz, 1H), 5.54 (s, 2H), 5.04 (s, 2H), 3.94-3.86 (m, 2H), 3.25 (dt, J=12.7, 2.2 Hz, 2H), 1.98 (dt, J=12.9, 4.4 Hz, 2H), 1.71 (d, J=12.5 Hz, 2H). LC/MS, m/z=440 [M+H]$^+$ (Calc: 439).

Example 6

Synthesis of Compound 1

Scheme 5

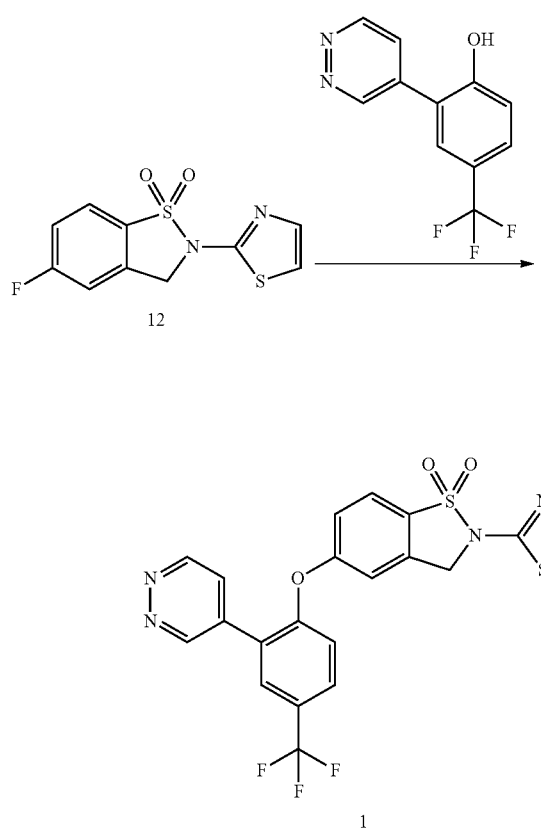

To a mixture of compound 12 (0.273 g, 1.01 mmol, 1 eq) in DMSO (2.0 mL) in a pressure reaction tube was added 2-(pyridazin-4-yl)-4-(trifluoromethyl)phenol (0.243 g, 1.01 mmol, 1 eq) and K$_2$CO$_3$ (0.280 g, 2.03 mmol, 2 eq). The reaction mixture was heated at 100° C. overnight then at 150° C. for 4 hours. When cooled, the reaction mixture was directly chromatographed over silica gel with 0-100% acetone in hexanes. The fractions containing the product were evaporated in vacuo and the residue purified a once more by reverse-phase chromatography (C18, acetonitrile/water with 0.1% TFA, 20-90%). The product fractions were frozen and lyophilized to yield compound 1 as a yellow-tan powder (0.007 g, 0.014 mmol, 1% yield). $^1$H NMR $\delta_H$ (400 MHz, DMSO-d$_6$) 9.49-9.47 (m, 1H), 9.29 (dd, J=5.3, 1.3 Hz, 1H), 8.14 (d, J=2.2 Hz, 1H), 7.96-7.90 (m, 2H), 7.82 (d, J=8.6 Hz, 1H), 7.43 (d, J=8.6 Hz, 1H), 7.38 (d, J=2.4 Hz, 1H), 7.33 (dd, J=8.6, 2.6 Hz, 1H), 7.22 (d, J=4.8 Hz, 1H), 6.95 (d, J=4.6 Hz, 1H), 5.60 (s, 2H). LC/MS, m/z=491 [M+H]$^+$ (Calc: 490).

Example 7

Synthesis of Compound 2

Scheme 6

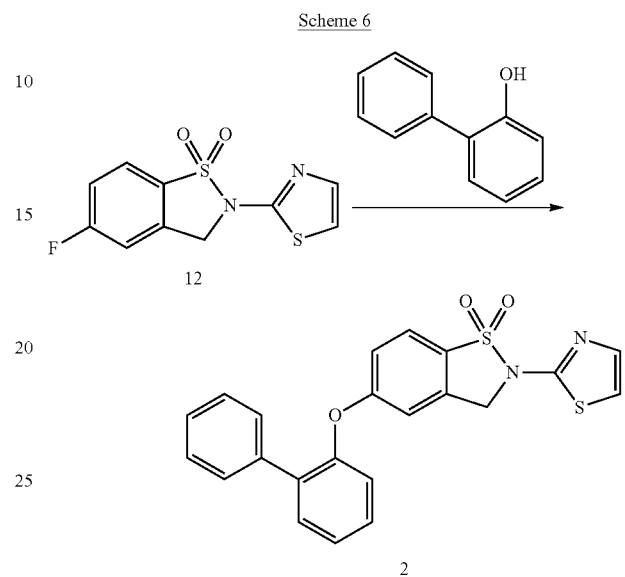

To a mixture of compound 12 (0.100 g, 0.370 mmol, 1 eq) in NMP (3.5 mL) in a pressure reaction tube was added [1,1'-biphenyl]-2-ol (0.096 g, 0.564 mmol, 1.5 eq) and K$_2$CO$_3$ (0.078 g, 0.564 mmol, 1.5 eq). The reaction mixture was heated at 100° C. for 3 days. When cooled, the reaction mixture was diluted with 75 mL brine and extracted three times with 25 mL EtOAc. The organics were dried over MgSO$_4$, filtered and concentrated in vacuo. The residue was chromatographed over silica gel with 50-100% EtOAc in hexanes. The product fractions were evaporated in vacuo then dried under vacuum at 40° C. to give compound 2 as a cream-colored powder (0.120 g, 0.285 mmol, 77% yield). $^1$H NMR $\delta_H$ (400 MHz, DMSO-d$_6$) 7.70 (d, J=8.6 Hz, 1H), 7.54 (dd, J=7.5, 1.8 Hz, 1H), 7.50-7.37 (m, 4H), 7.36-7.30 (m, 2H), 7.29-7.22 (m, 3H), 7.12 (d, J=2.4 Hz, 1H), 7.02 (dd, J=8.6, 2.4 Hz, 1H), 6.93 (d, J=4.8 Hz, 1H), 5.55 (s, 2H). LC/MS, m/z=421 [M+H]$^+$ (Calc: 420).

Example 8

Synthesis of Compound 6

Scheme 8

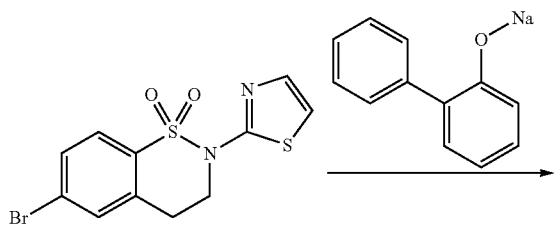

-continued

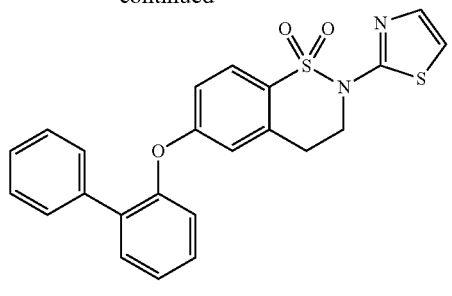

6

To a mixture of compound 18 (0.173 g, 0.501 mmol, 1 eq), sodium [1,1'-biphenyl]-2-olate (0.106 g, 0.552 mmol, 1.1 eq), Pd(dba)$_2$ (0.015 g, 0.026 mmol, 0.05 eq), and Q-Phos (0.037 g, 0.052 mmol, 0.1 eq) in a pressure reaction tube was added toluene (2.5 mL). The reaction was stirred at ambient temperature for 2 hours, heated at 40° C. overnight, heated at 50° C. for 2 hours, the heated at 70° C. overnight. The reaction mixture was evaporated in vacuo and the residue chromatographed over silica gel with 0-40% EtOAc in hexanes. The product fractions were evaporated in vacuo. The residue thus obtained was repeatedly extracted with warm hexanes and the pooled hexane extracts were concentrated to near dryness. Additional fresh hexanes was added to bring the volume to ~1-2 mL. The solids were filtered off, rinsed with 1 mL of hexanes and dried under vacuum at 40° C. to give compound 6 as a light tan crystalline powder (0.066 g, 0.152 mmol, 30% yield). $^1$H NMR $\delta_H$ (400 MHz, DMSO-d$_6$) 7.76 (d, J=8.8 Hz, 1H), 7.56-7.49 (m, 2H), 7.49-7.41 (m, 3H), 7.41-7.32 (m, 4H), 7.31-7.25 (m, 1H), 7.18 (dd, J=7.9, 1.1 Hz, 1H), 6.91 (d, J=2.4 Hz, 1H), 6.87 (dd, J=8.8, 2.4 Hz, 1H), 4.53 (t, J=6.1 Hz, 2H), 3.20 (t, J=6.1 Hz, 2H). LC/MS, m/z=435 [M+H]$^+$ (Calc: 434).

Example 9

Synthesis of Compound 3

Scheme 8

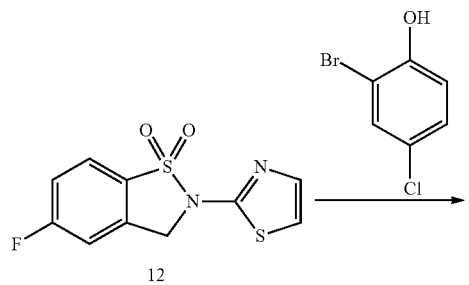

-continued

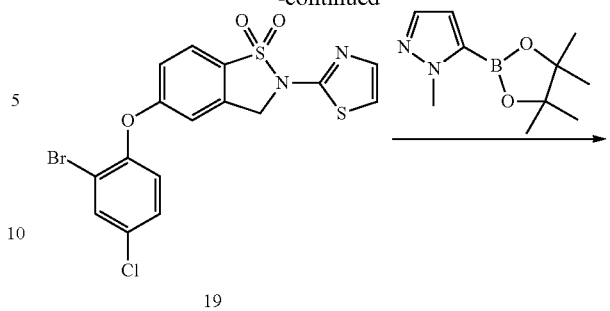

19

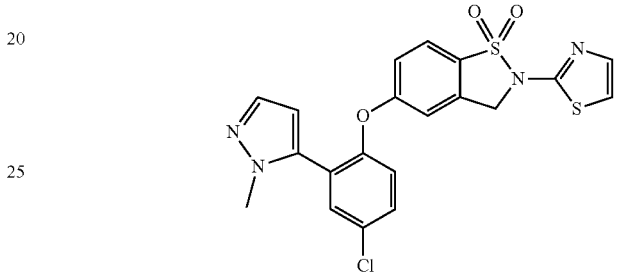

3

To a mixture of compound 12 (0.201 g, 0.744 mmol, 1 eq) in NMP (7.0 mL) in a pressure reaction tube was added 2-bromo-4-chlorophenol (0.233 g, 1.12 mmol, 1.5 eq) and K$_2$CO$_3$ (0.153 g, 1.11 mmol, 1.5 eq). The reaction was heated at 100° C. for 5 days. When cooled, the reaction mixture was diluted with 75 mL brine and extracted three times with 25 mL EtOAc. The combined organics were washed once with 25 mL brine, dried over Na$_2$SO$_4$, filtered and evaporated in vacuo. The residue was chromatographed over silica gel with 30-100% EtOAc in hexanes. The product fractions were evaporated in vacuo to give compound 19 as an off-white solid (0.122 g, 0.267 mmol, 36% yield). LC/MS, m/z=457 [M+H]$^+$ (Calc: 456).

To a mixture of compound 19 (0.122 g, 0.267 mmol, 1 eq) in dioxane (5.0 mL) was added 1-methyl-5-(4,4,5,5-tetramethyl-1,3,2-dioxaborolan-2-yl)-1H-pyrazole (0.065 g, 0.312 mmol, 1.2 eq), 2M Na$_2$CO$_3$ solution (0.27 mL, 0.54 mmol, 2 eq) and PdCl$_2$(dppf) (0.016 g, 0.020 mmol, 0.07 eq). The reaction was heated at reflux overnight. When cooled, the reaction mixture was partitioned between 25 mL EtOAc and 25 mL brine. The organics were isolated, dried over Na$_2$SO$_4$, filtered and concentrated in vacuo. The residue was chromatographed over silica gel with 25-75% acetone in hexanes. The product fractions were evaporated in vacuo to give compound 3 as a light tan powder (0.095 g, 0.21 mmol, 78% yield). $^1$H NMR $\delta_H$ (400 MHz, DMSO-d$_6$) 7.70 (d, J=8.6 Hz, 1H), 7.67-7.61 (m, 2H), 7.36 (d, J=8.6 Hz, 1H), 7.31 (d, J=2.0 Hz, 1H), 7.20 (d, J=4.8 Hz, 1H), 7.13-7.07 (m, 2H), 6.93 (d, J=4.8 Hz, 1H), 6.24 (d, J=2.0 Hz, 1H), 5.55 (s, 2H), 3.70 (s, 3H). LC/MS, m/z=459 [M+H]$^+$ (Calc: 458).

Example 10

Synthesis of Compound 7

Scheme 9

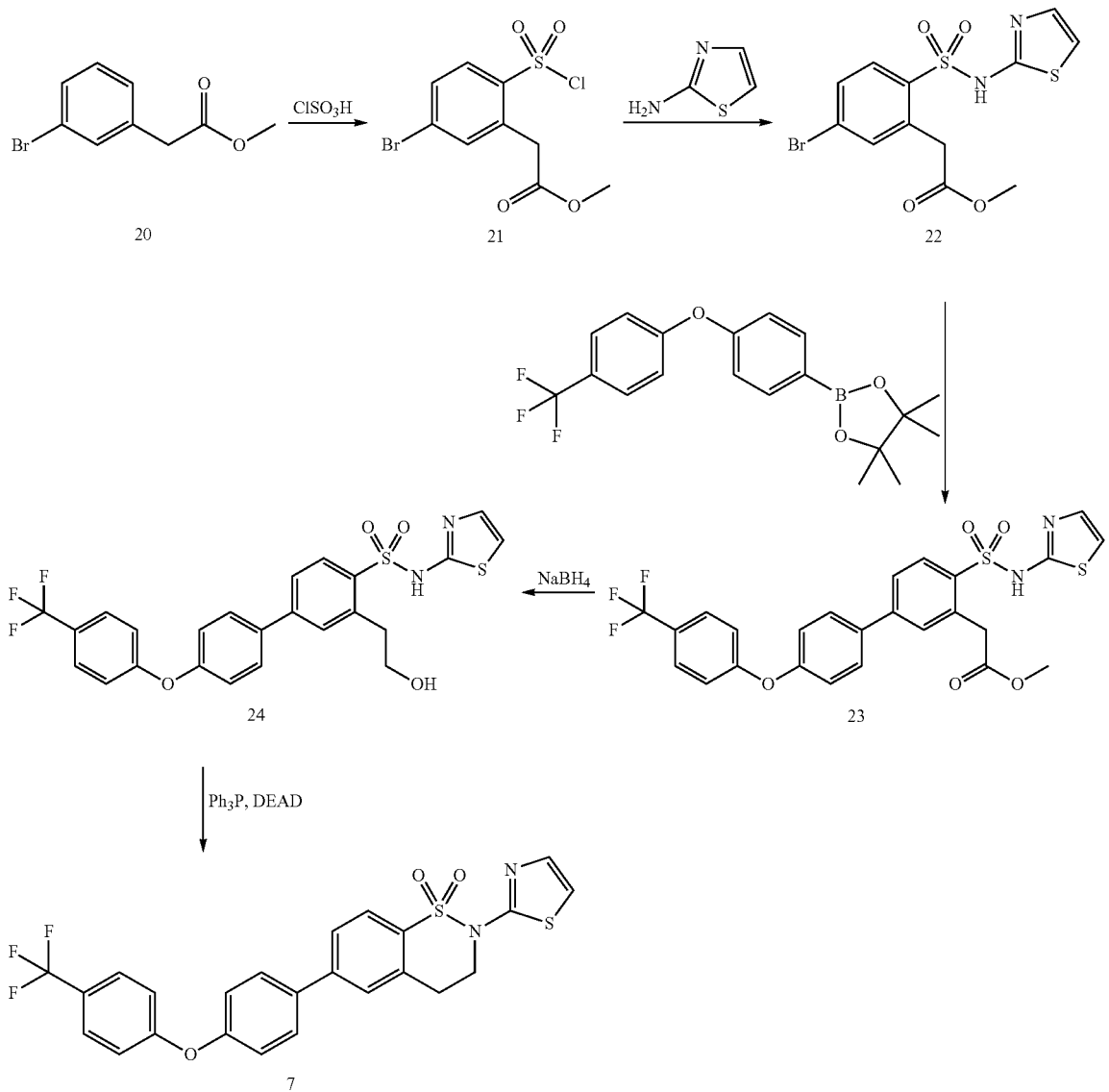

Compound 20 (11.467 g, 50.06 mmol, 1 eq) was cooled on an ice-salt bath. To this was added chlorosulfonic acid (30 mL, 450 mmol, 9 eq) dropwise over ~50 minutes. The ice bath was allowed to melt and the reaction warmed up and stirred for 4 days. The reaction mixture was then carefully poured onto ~500 g ice chips. The resulting solid was collected by filtration and rinsed with additional water. The solid was partially air-dried then dissolved in 100 mL DCM, dried with MgSO$_4$, filtered and evaporated in vacuo to give compound 21 as a yellow-tan solid (12.446 g, 37.99 mmol, 76% yield). LC/MS, m/z=327 [M+H]$^+$ (Calc: 326).

To a mixture of compound 21 (12.446 g, 37.99 mmol, 1 eq) and 2-aminothiazole (7.609 g, 76.98 mmol, 2 eq) was added 1:1 pyridine/DCM (100 mL). The mixture was heated at reflux for 3 hours then evaporated in vacuo. The residue was partitioned between 50 mL EtOAc and 50 mL 1N HCl which caused a solid to form. The solid was collected via filtration and washed once with 10 mL EtOAc and once with 25 mL water then once more with 10 mL EtOAc. The material was dried under vacuum at 40° C. to give compound 22 as a tan powder (3.437 g, 8.78 mmol, 23% yield). LC/MS, m/z=391 [M+H]$^+$ (Calc: 390).

To a mixture of compound 22 (0.392 g, 1.00 mmol, 1 eq) in dioxane (5.0 mL) in a pressure reaction tube was added 4,4,5,5-tetramethyl-2-(4-(4-(trifluoromethyl)phenoxy)phenyl)-1,3,2-dioxaborolane (0.406 g, 1.11 mmol, 1.1 eq), 2N Na$_2$CO$_3$ solution (1.0 mL, 2.0 mmol, 2 eq), and PdCl$_2$(dppf) (0.044 g, 0.054 mmol, 0.05 eq). The reaction was sealed and heated at 80° C. overnight. After cooling, the reaction mixture was diluted into 30 mL 10% citric acid solution and extracted once with 50 mL DCM. The organics were dried over Na$_2$SO$_4$, filtered and evaporated in vacuo to give compound 23 which was carried on as-is. LC/MS, m/z=549 [M+H]$^+$ (Calc: 548).

To a solution of compound 23 (assume 1.00 mmol) in THF (25 mL) was added NaBH$_4$ (0.269 g, 7.11 mmol) and MeOH (2.5 mL). The reaction mixture was heated at reflux for 4 hours then additional NaBH$_4$ (1.007 g, 26.62 mmol) was added. After refluxing overnight, additional NaBH$_4$ (0.989 g, 26.14 mmol) and MeOH (2.5 mL) were added. After 1 hour, more MeOH (2.5 mL) was added. After an additional hour more, MeOH (2.5 mL) was added. After 4 hours, more NaBH$_4$ (1.007 g, 26.62 mmol) and MeOH (2.5 mL) were added. After refluxing one more night, the reaction was cooled. After cooling to ambient temperature the reaction mixture was diluted into 100 mL 10% citric acid solution, 25 mL brine was added and the mixture extracted with 100 mL EtOAc. The organics were isolated and washed once with 25 mL brine. The organics were dried over Na$_2$SO$_4$, filtered and evaporated in vacuo to give compound 24 which was carried on as-is. LC/MS, m/z=521 [M+H]$^+$ (Calc: 520).

To a mixture of triphenyl phosphine (0.315 g, 1.20 mmol, 1.2 eq) in THF (5.0 mL) was added DEAD (0.55 mL, 40% solution in toluene, 1.21 mmol, 1.2 eq). The reaction was stirred for 2 minutes then added to a solution of compound 24 (assume 1.00 mmol, 1 eq) in THF (10.0 mL). After 1.5 hours, to a mixture of triphenyl phosphine (0.159 g, 0.61 mmol, 0.6 eq) in THF (2.0 mL) was added DEAD (0.28 mL, 40% solution in toluene, 0.62 mmol, 0.6 eq). This was stirred for 1 minute then added to the main reaction mixture. The reaction was stirred for 30 minutes then evaporated in vacuo. The residue was chromatographed over silica gel with 0-40% EtOAc in hexanes. The product fractions were evaporated in vacuo and the residue dried under vacuum at 50° C. to give compound 7 as an off-white glassy solid (0.160 g, 0.318 mmol, 32% yield). $^1$H NMR δ$_H$ (400 MHz, DMSO-d$_6$) 7.92 (d, J=8.8 Hz, 1H), 7.84-7.74 (m, 6H), 7.54 (d, J=3.5 Hz, 1H), 7.40 (d, J=3.7 Hz, 1H), 7.28-7.19 (m, 4H), 4.64 (t, J=6.1 Hz, 2H), 3.39 (t, J=6.1 Hz, 2H). LC/MS, m/z=503 [M+H]$^+$ (Calc: 502).

Example 10

Biological Testing

Representative Compounds of the Invention have been tested in the FLIPR®, FLIPR$^{TETRA}$®, and/or electrophysiology (EP) assays for sodium channel blocking activity, which is described in detail above. Representative values are presented in TABLE 4.

TABLE 4

| Evaluation of compounds as sodium channel (Na$_v$) blockers | |
|---|---|
| Compound Example No. | Na$_v$1.7 FLIPR assay IC$_{50}$ (μM) |
| 1 | 1.741 |
| 2 | >20 |
| 3 | 9.102 |
| 4 | 1.384 |
| 5 | 0.766 |
| 6 | 1.704 |
| 7 | 7.088 |

Having now fully described this disclosure, it will be understood by those of ordinary skill in the art that the same can be performed within a wide and equivalent range of conditions, formulations and other parameters without affecting the scope of the disclosure or any embodiment thereof

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference in their entirety.

What is claimed is:

1. A compound having Formula I:

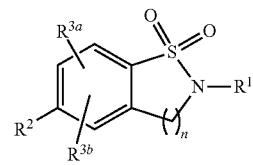

or a pharmaceutically acceptable salt or solvate thereof, wherein:
R$^1$ is optionally substituted thiazolyl;
R$^2$ is selected from the group consisting of:

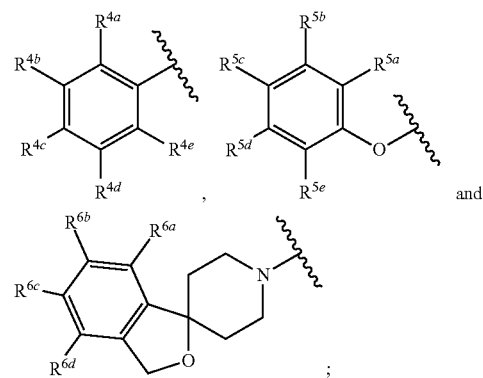

R$^{3a}$ and R$^{3b}$ are each independently selected from the group consisting of hydrogen and halogen;
R$^{4a}$, R$^{4b}$, R$^{4d}$, and R$^{4e}$ are each independently selected from the group consisting of hydrogen, alkyl, halo, nitro, cyano, hydroxy, amino, alkylamino, dialkylamino, haloalkyl, monohydroxyalkyl, dihydroxyalkyl, alkoxy, haloalkoxy, carboxy, and alkoxycarbonyl;
R$^{4c}$ is selected from the group consisting of aryloxy and heteroaryloxy;
R$^{5a}$ is selected from the group consisting of optionally substituted aryl and optionally substituted heteroaryl;
R$^{5b}$, R$^{5c}$, R$^{5d}$, and R$^{5e}$ are each independently selected from the group consisting of hydrogen, alkyl, halo, nitro, cyano, hydroxy, amino, alkylamino, dialkylamino, haloalkyl, monohydroxyalkyl, dihydroxyalkyl, alkoxy, haloalkoxy, carboxy, and alkoxycarbonyl;
R$^{6a}$, R$^{6b}$, R$^{6c}$, and R$^{6d}$ are each independently selected from the group consisting of hydrogen, alkyl, halo, nitro, cyano, hydroxy, amino, alkylamino, dialkylamino, haloalkyl, monohydroxyalkyl, dihydroxyalkyl, alkoxy, haloalkoxy, carboxy, and alkoxycarbonyl; and n is 1, 2, or 3.

2. The compound of claim 1, wherein $R^{3a}$ and $R^{3b}$ are hydrogen, or a pharmaceutically acceptable salt or solvate thereof.

3. The compound of claim 1, wherein n is 1, or a pharmaceutically acceptable salt or solvate thereof.

4. The compound of claim 1, wherein n is 2, or a pharmaceutically acceptable salt or solvate thereof.

5. The compound of claim 1, wherein $R^1$ is optionally substituted 2-thiazolyl, or a pharmaceutically acceptable salt or solvate thereof.

6. The compound of claim 1, wherein:
$R^2$ is:

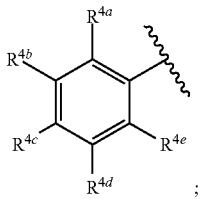

$R^{4c}$ is selected from the group consisting of aryloxy and heteroaryloxy; and
$R^{4a}$, $R^{4b}$, $R^{4d}$, and $R^{4e}$ are each independently selected from the group consisting of hydrogen and halo,
or a pharmaceutically acceptable salt or solvate thereof.

7. The compound of claim 6, wherein $R^2$ is:

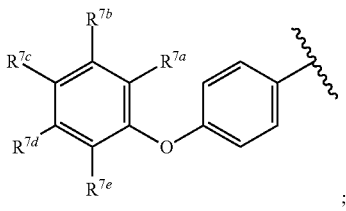

and
$R^{7a}$, $R^{7b}$, $R^{7c}$, $R^{7d}$, and $R^{7e}$ are each independently selected from the group consisting of hydrogen, alkyl, halo, nitro, cyano, hydroxy, amino, alkylamino, dialkylamino, haloalkyl, monohydroxyalkyl, dihydroxyalkyl, alkoxy, haloalkoxy, carboxy, and alkoxycarbonyl, or a pharmaceutically acceptable salt or solvate thereof.

8. The compound of claim 1, wherein:
$R^2$ is:

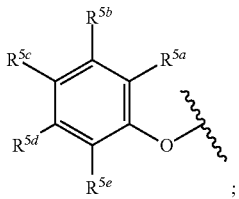

and
$R^{5b}$, $R^{5c}$, $R^{5d}$, and $R^{5e}$ are each independently selected from the group consisting of hydrogen, alkyl, halo, cyano, hydroxy, alkoxy, and haloalkoxy, or a pharmaceutically acceptable salt or solvate thereof.

9. The compound of claim 8, wherein $R^{5a}$ is optionally substituted phenyl, or a pharmaceutically acceptable salt or solvate thereof.

10. The compound of claim 1, wherein $R^2$ is:

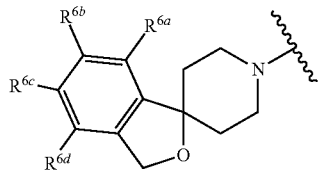

or a pharmaceutically acceptable salt or solvate thereof.

11. The compound of claim 10, wherein $R^{6a}$, $R^{6b}$, $R^{6c}$, and $R^{6d}$ are each hydrogen, or a pharmaceutically acceptable salt or solvate thereof.

12. The compound of claim 1 selected from the group consisting of:
- 5-(2-(pyridazin-4-yl)-4-(trifluoromethyl)phenoxy)-2-(thiazol-2-yl)-2,3-dihydrobenzo-[d]isothiazole 1,1-dioxide;
- 5-([1,1'-biphenyl]-2-yloxy)-2-(thiazol-2-yl)-2,3-dihydrobenzo[d]isothiazole 1,1-dioxide;
- 5-(4-chloro-2-(1-methyl-1H-pyrazol-5-yl)phenoxy)-2-(thiazol-2-yl)-2,3-dihydrobenzo-[d]isothiazole 1,1-dioxide;
- 5-(3H-spiro[isobenzofuran-1,4'-piperidin]-1'-yl)-2-(thiazol-2-yl)-2,3-dihydrobenzo[d]isothiazole 1,1-dioxide;
- 6-(3H-spiro[isobenzofuran-1,4'-piperidin]-1'-yl)-2-(thiazol-2-yl)-3,4-dihydro-2H-benzo[e][1,2]thiazine 1,1-dioxide;
- 6-([1,1'-biphenyl]-2-yloxy)-2-(thiazol-2-yl)-3,4-dihydro-2H-benzo[e][1,2]thiazine 1,1-dioxide; and
- 2-(thiazol-2-yl)-6-(4-(4-(trifluoromethyl)phenoxy)phenyl)-3,4-dihydro-2H-benzo[e][1,2]thiazine 1,1-dioxide, or a pharmaceutically acceptable salt or solvate thereof.

13. A pharmaceutical composition comprising the compound of claim 1, or a pharmaceutically acceptable salt or solvate thereof, and a pharmaceutically acceptable carrier.

14. A method of treating pain in a mammal, comprising administering an effective amount of a compound as claimed in claim 1, or a pharmaceutically acceptable salt or solvate thereof, to a mammal in need of such treatment.

15. The method of claim 14, wherein said method is for preemptive or palliative treatment of pain.

16. The method of claim 14, wherein said pain is selected from the group consisting of chronic pain, inflammatory pain, neuropathic pain, acute pain, and surgical pain.

17. A method of modulating $Na_v1.7$ sodium channels in a mammal, comprising administering to the mammal a modulating-effective amount of at least one compound as claimed in claim 1, or a pharmaceutically acceptable salt or solvate thereof.

18. The compound as claimed in claim 1, wherein said compound is $^3H$, $^{11}C$, or $^{14}C$ radiolabeled, or a pharmaceutically acceptable salt or solvate thereof.

19. The compound as claimed in claim 8, wherein $R^{5a}$ is optionally substituted heteroaryl, or a pharmaceutically acceptable salt or solvate thereof.

20. A method of modulating sodium channels in vitro, comprising administering to a cell a modulating-effective amount of a compound as claimed in claim 1, or a pharmaceutically acceptable salt or solvate thereof.

21. The method of claim 20, wherein the compound, or a pharmaceutically acceptable salt or solvate thereof, blocks $Na_v1.7$ sodium channels in the cell.

* * * * *